US007745225B2

(12) United States Patent
Mitts et al.

(10) Patent No.: US 7,745,225 B2
(45) Date of Patent: Jun. 29, 2010

(54) PROGNOSTIC TESTS FOR DEVELOPMENT OF DERMAL STRETCH MARKS AND IMPLICATIONS FOR THE PREVENTIVE TREATMENT THEREOF

(75) Inventors: Thomas Mitts, Visalia, CA (US); Felipe Jimenez, Seal Beach, CA (US); Aleksander Hinek, Toronto (CA)

(73) Assignees: Human Matrix Sciences, LLC, Visalia, CA (US); The Hospital For Sick Children, Toronto, Ontario (CA)

( * ) Notice: Subject to any disclaimer, the term of this patent is extended or adjusted under 35 U.S.C. 154(b) by 257 days.

(21) Appl. No.: 11/141,635

(22) Filed: May 31, 2005

(65) Prior Publication Data

US 2006/0040252 A1    Feb. 23, 2006

Related U.S. Application Data

(60) Provisional application No. 60/575,737, filed on May 28, 2004.

(51) Int. Cl.
  *C12P 19/24* (2006.01)
  *C12P 19/42* (2006.01)
  *C12Q 1/70* (2006.01)
  *C12Q 1/68* (2006.01)
(52) U.S. Cl. .............................. 436/94; 436/86; 435/5; 435/6
(58) Field of Classification Search ........................ None
  See application file for complete search history.

(56) References Cited

U.S. PATENT DOCUMENTS

| 5,514,709 A * | 5/1996 | Counts et al. ................ 514/461 |
| 2004/0162232 A1 | 8/2004 | Mitts et al. |
| 2005/0208150 A1 | 9/2005 | Mitts et al. |

FOREIGN PATENT DOCUMENTS

| WO | WO 01/07006 A | 2/2001 |
| WO | WO 01/17486 A | 3/2001 |

OTHER PUBLICATIONS

Pepe et al. (Am J. Epidemiology, 2004, vol. 159, pp. 882-890).*
Pieraggi, et al.; *Striae: Morphological Aspects of Connective Tissue*; Virchows Arch; 1982; 396:279-289.
Lee, et al.; *Decreased Expression of Collagen and Fibronectin Genes in Striase Distensae Tissue*; Clinical and Experimental Dermatology; 1994; 19-285-288.
Watson, et al.; *Fibrillin Microfibrils are Reduced in Skin Exhibiting Striae Distensae*; British Journal of Dermatology; 1998; 138: 931-937.
Pierard, et al.; *Tensile Properties of Relaxed Excised Skin Exhibiting Striae Distensae*; Journal of Medical Engineering & Technology, vol. 23, No. 2, (Mar./Apr. 1989); pp. 69-72.
Kang, et al.; *Topical Tretinoin (Retinoic Acid) Improves Early Stretch Marks*; Arch Derm. vol. 132, May 1996; pp. 519-526.
Viennet, et al.; *Mechanical Benefit of Striae Distensae Fibroblasts included in Collagen Lattices*; Journal de la Societe de Biologie; 195 (4), 427-430 (2001) English Abstract on p. 427.
Cohen-Letessier; *A Disorder of Fibroblasts? Aetiologic Theories*; Nouv. Dermatol. 1998; 17:431-435; English Abstract on p. 434.

* cited by examiner

*Primary Examiner*—Sarae Bausch
*Assistant Examiner*—Katherine Salmon
(74) *Attorney, Agent, or Firm*—Pepper Hamilton LLP

(57) ABSTRACT

Various methods of assessing the regenerative potential of dermal tissue in a patient may be determined and methods to determine the potential development of stretch marks in a patient are provided. Through the analysis of a series of dermal tissue samples, a method of monitoring the aging process of the dermal tissue of a patient is possible. Damaged or stretched marked skin may also be used in the development of various diagnostic therapies relating to the inducement of the extracellular matrix components of the skin due to the loss of elastic fibers generally found in stretch marked skin.

7 Claims, 14 Drawing Sheets
(11 of 14 Drawing Sheet(s) Filed in Color)

FIGURE 3
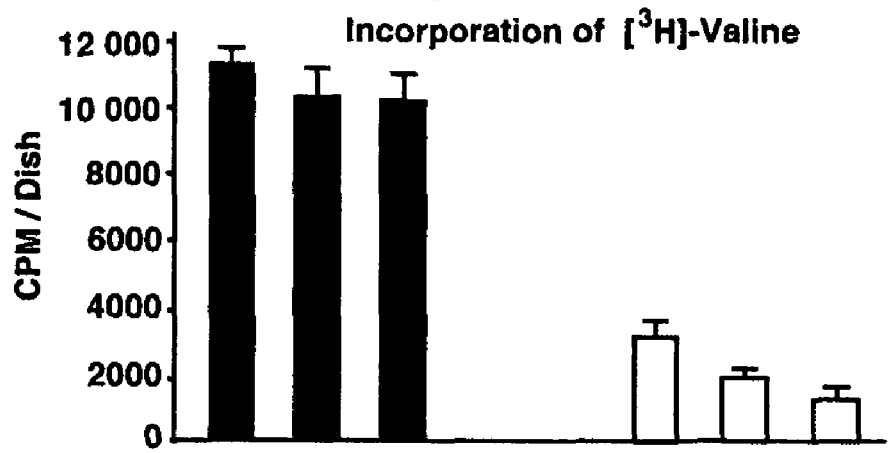
3A Deposition of Insoluble Elastin in 7 day-old Primary Cultures of Dermal Fibroblasts
Incorporation of [³H]-Valine
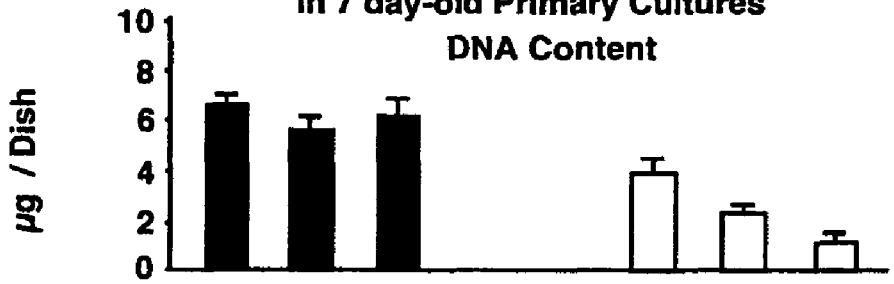
3B Proliferation of Dermal Fibroblasts in 7 day-old Primary Cultures
DNA Content
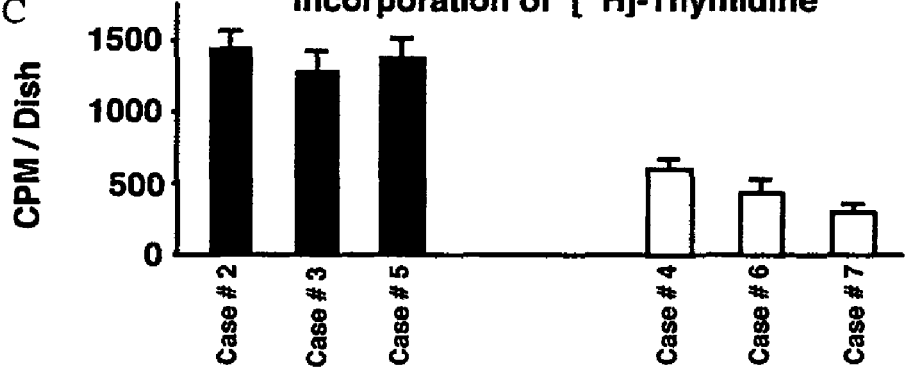
3C Incorporation of [³H]-Thymidine FIGURE 4
A  Fibroblasts taken from patient with the Stretch Marks Migrate slower than Fibroblasts from normal Skin
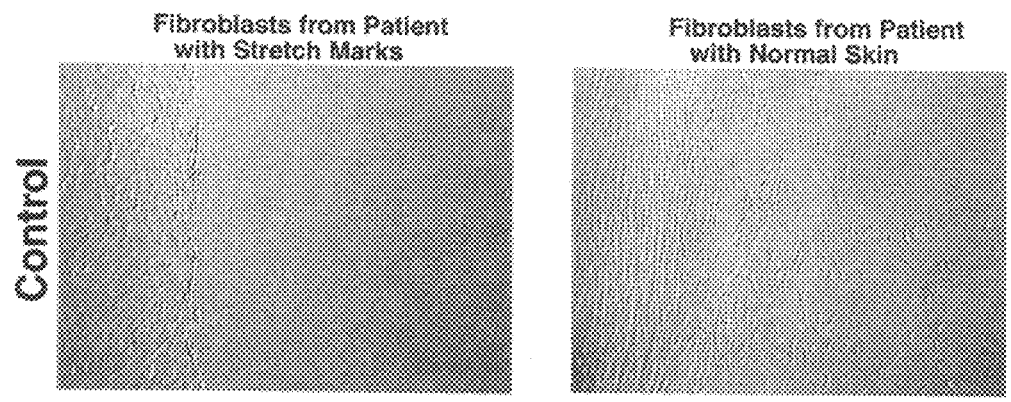
B  ProK-60 Stimulate Migration of Fibroblasts from Both patients
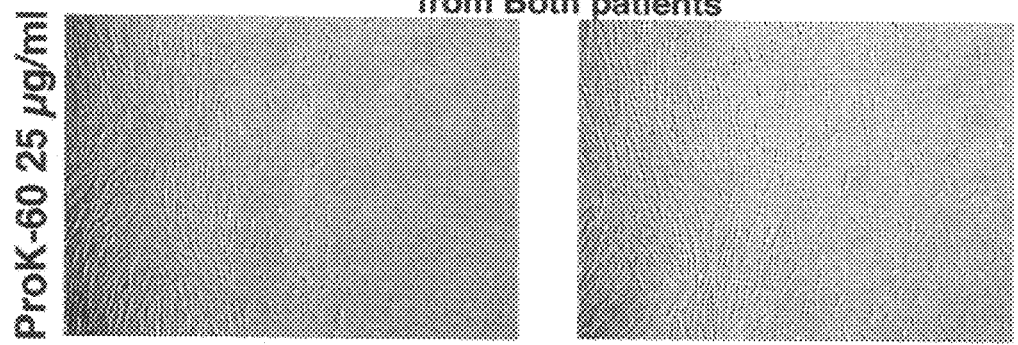
3 days in Culture Figure 5
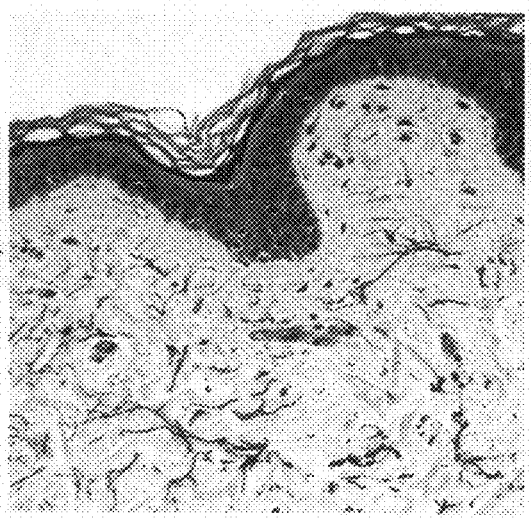
Normal Skin
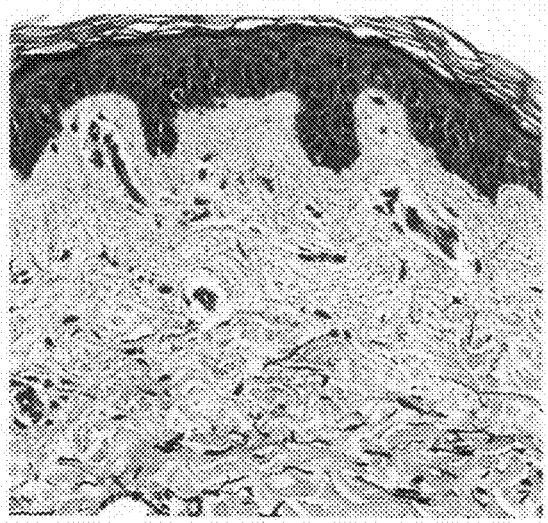
Normally-looking Skin Patient with Stretch Marks
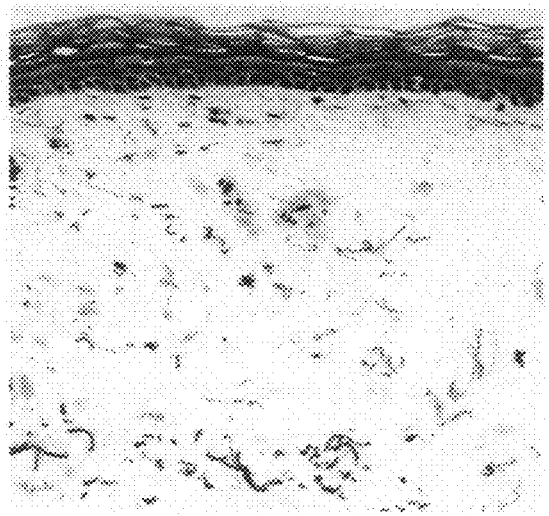
Stretch Mark

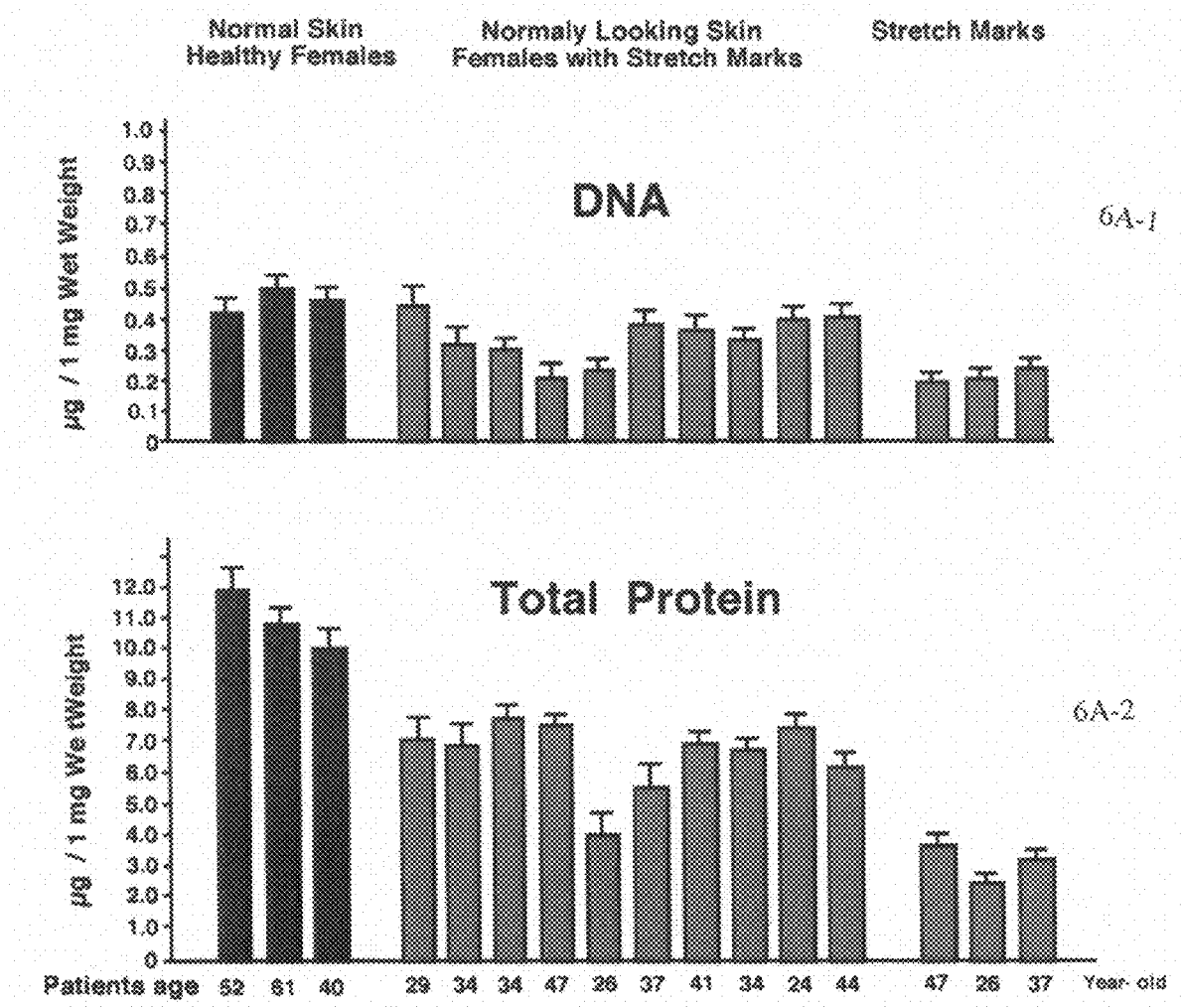

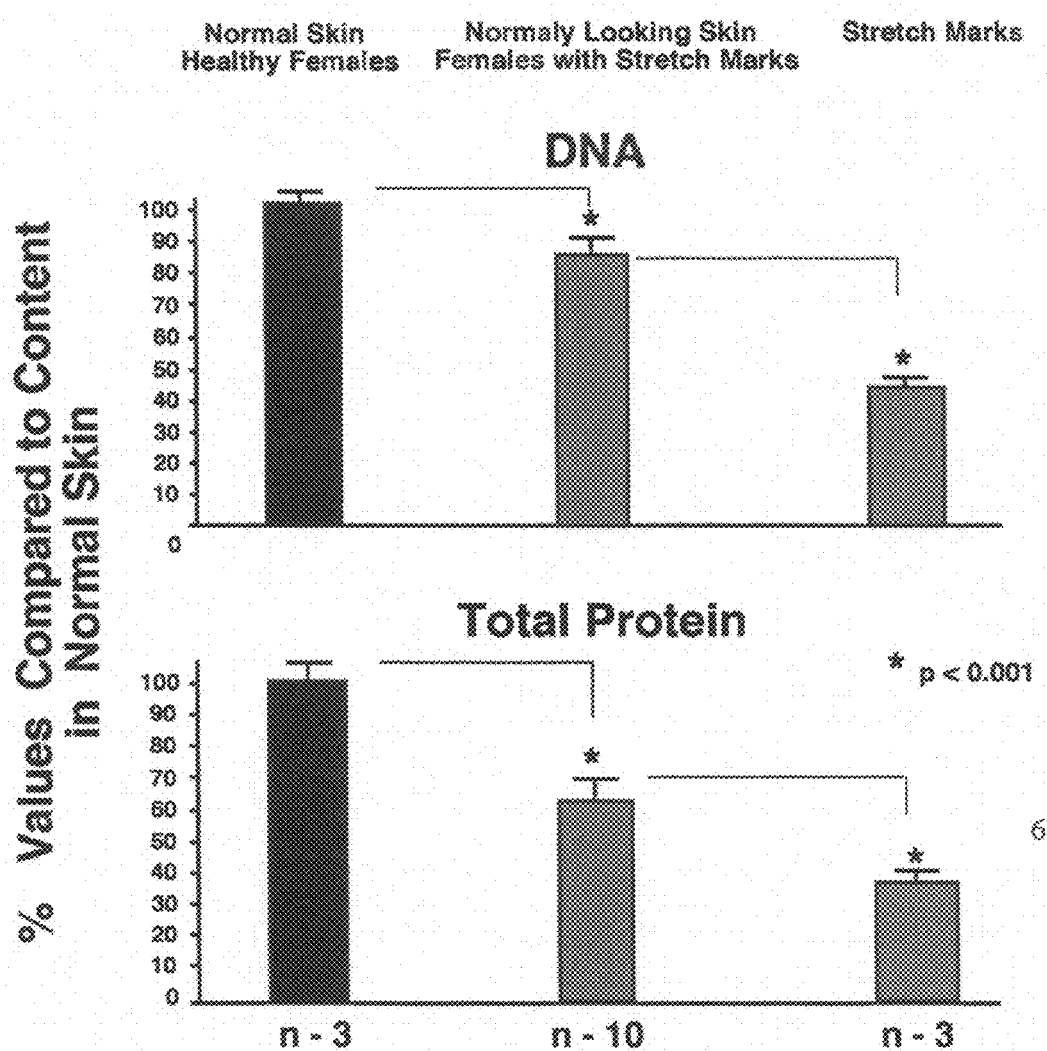

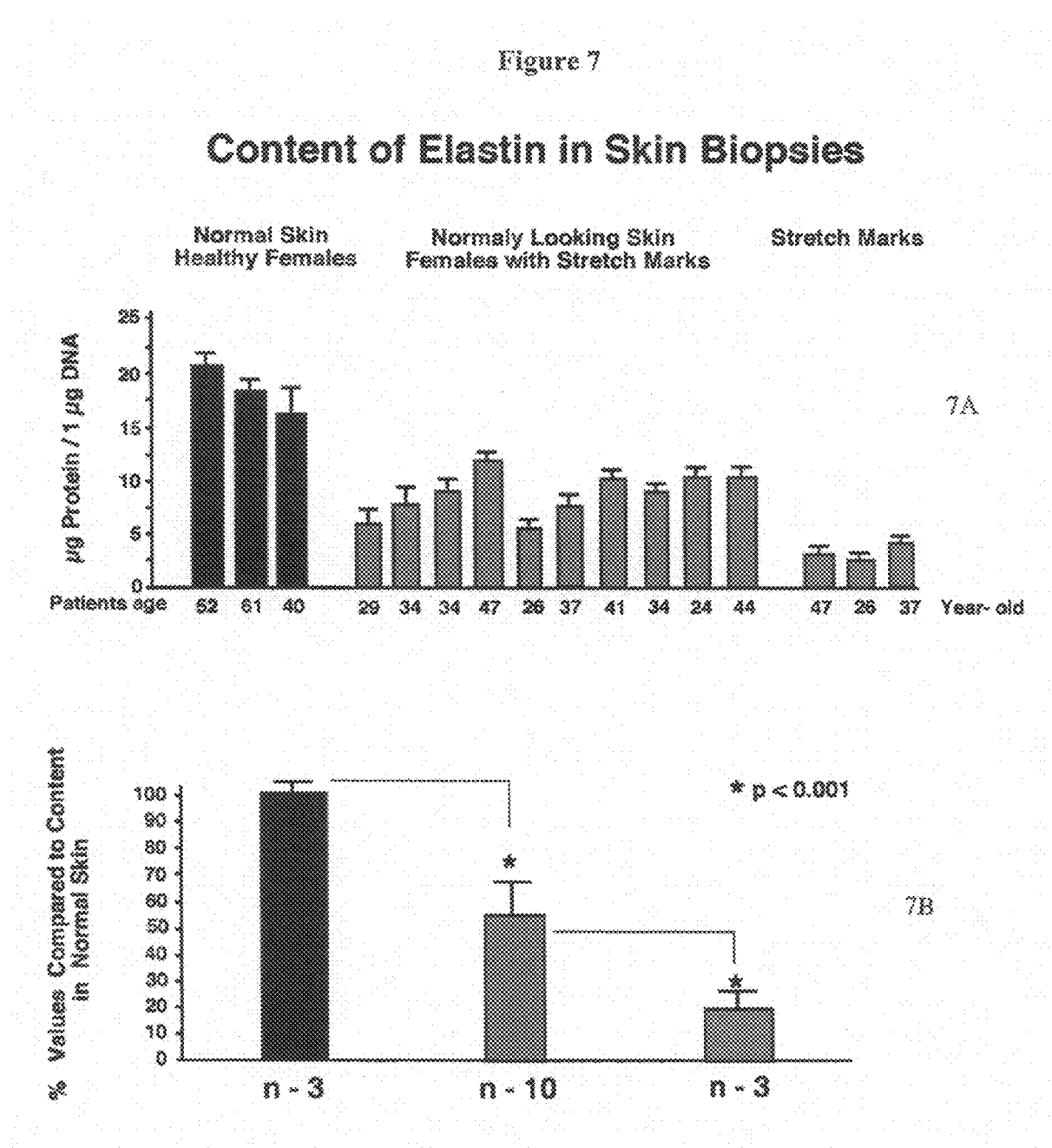

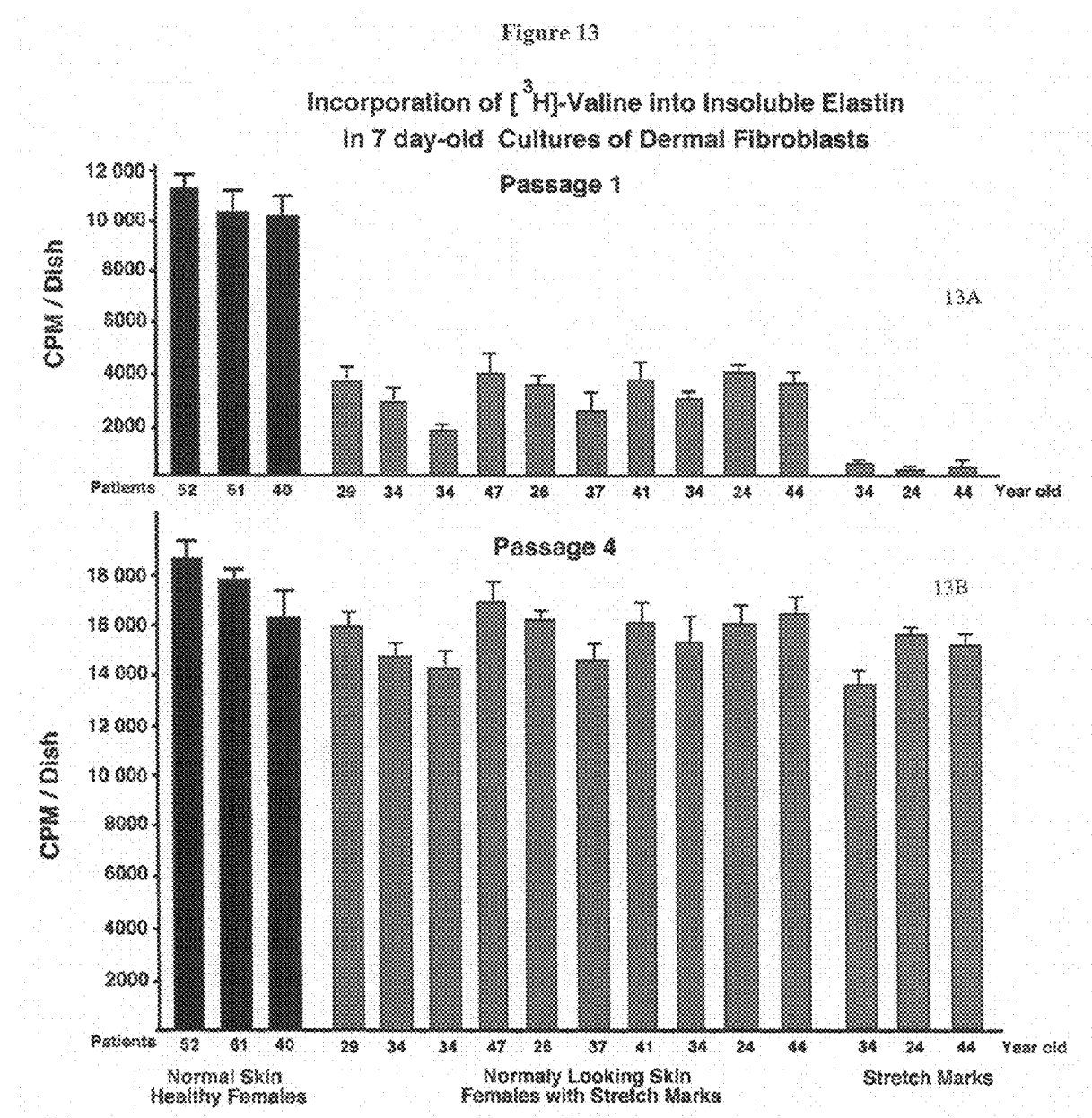

PROGNOSTIC TESTS FOR DEVELOPMENT OF DERMAL STRETCH MARKS AND IMPLICATIONS FOR THE PREVENTIVE TREATMENT THEREOF

CROSS REFERENCE TO RELATED APPLICATIONS

This application claims priority to and incorporates herein by reference U.S. Provisional Application No. 60/575,737 filed on May 28, 2004 titled "Prognostic tests for development of dermal stretch marks and implications for the preventive treatment thereof".

FIELD

The present invention relates to the treatment and prevention of damaged or stretch marked skin.

BACKGROUND

Elastin is an amorphous protein present in the elastic fibers of tissues such as arteries, blood vessels, skin, tendons and elastic ligaments, the abdominal wall, and lungs. Unlike other fibrous tissues like collagen, elastin is unique in that it may be stretched to over 150 percent of its original length but it can rapidly return to its original size and shape. This property of elastin provides tissues that incorporate it, the required ability to resume their original form after stretching due to blood flow, breathing, or bending. Like collagen protein, elastin contains about 30% glycine amino acid residues and is rich in proline. Elastin differs from collagen in that it contains very little hydroxyproline and no hydroxylysine. Elastin has a very high content of alanine and also contains two unique amino acids isodesmosine and desmosine. These amino acids are believed to be responsible for elastin's ability to return to its original shape after stretching.

Tropoelastin is a soluble precursor of elastin; it is a peptide with a molecular weight in the range of 70-75 kDa, it is synthesized by dermal fibroblasts and secreted in association with the 67 kDa elastin binding protein (EBP). EBP acts as a molecular chaperone protecting the highly hydrophobic tropoelastin molecules from intracellular self-aggregation and premature degradation and facilitating their proper assembly on the microfibrillar scaffold in the extracellular space. In the arterial tissues tropoelastin is produced and secreted into the extacellular space by smooth muscle cells; in other tissues it is produced in cells, like fibroblast cells, and is also secreted into the extracellular space. In these cells tropoelastin is synthesized by ribosomes in the rough endoplasmatic reticulum and processed by the Golgi apparatus. The soluble tropoelastin molecules secreted (often referred to a proelastin before secretion) into the extracellular space synthesize to form Elastin filaments and sheets via cross linking of the tropoelastin molecules primarily by crosslinking of lysine amino acid residues to form desmosine and isodesmosine. Mature elastin is amorphous and contains many cross links which makes it nearly impossible to solublize.

The resiliency of skin is maintained by elastic fibers in the extracellular matrix (ECM). These ECM components are organized into a networks of rope-like structures and composed of two major components: an amorphous core, consisting of extensively crosslinked elastin which makes up the bulk (>90%) of the fiber; and the 10-12-nm microfibrils made up of several distinct glycoproteins.

In various tissue or biological functions, inelastic collagen fibers may be interwoven with the elastin to limit stretching of the elastin and prevent tearing of elastin comprising tissue. Elastic fibers may also contain glycoproteins as microfibrils, which may serve to organize tropoelastin molecules secreted into the extracellular space for later crosslinking. Examples of such glycoproteins include laminin, which is a large glycoprotein and a major component of basement membranes and is made by all epithelial cells, and fibronectin which is a cell-surface and blood glycoprotein involved in a variety of cell surface phenomena.

Combinations of components of the extracellular matrix have been incorporated into cosmetic compositions. Elastin is insoluble due to its high degree of cross linking at its lysine residues and also because of its high content (about 75%) of hydrophobic amino acids (Gly, Val, Ala, Pro). In some instances, normally cross-linked insoluble elastin (i.e., insoluble in water, organic solvents, and physiological fluids such as saline and blood) is rendered soluble using a variety of chemical and enzymatic methods to cleave insoluble elastin protein and form smaller peptide fragments.

The human skin consists of two layers; a superficial layer called the epidermis which is epithelial tissue and a deeper layer called the dermis that is primarily connective tissue. These two layers are bound together to form skin which varies in thickness from less than about 0.5 mm, to 3 or even 4 millimeters. The main types of proteins that make up the matrix include collagens, Elastin, fibronectin and laminin. Normal elastic fiber assembly is visualized as a spider web spanning the dermis. Exposure of the skin to ultraviolet and visible light from the sun, wind, and chemicals leads to loss of moisture in the epidermal layers and degradation of the elastin present in the skin. Loss of elasticity in skin primarily occurs because of an over-production of poorly assembled elastic fibers induced by exposure to sunlight. These poorly assembled elastic fibers can be visualized as "clumps" in the dermoepidermal junction and papillary dermis and is commonly referred to as solar elastosis. These effects, result in loss of skin elasticity, tone and texture, are collectively referred to as aging of the skin. Loss of elasticity in elastic tissues such as arteries is mainly due to calcification and glycation of elastic fibers.

Stretch marks, also known as striae gravidarum, or 'striae', are the lines that appear on the skin which are caused by a breaking of the elastic layer of the epidermis. Skin is composed of two layers, as described above. Stretch marks occur in the dermis, the resilient layer that helps skin retain its shape. As a result of this layer being constantly stretched over time it breaks down and becomes less and less elastic and the small connective fibers within it break. Striae may take many forms and colors, from almost invisible tiny lines to deep red lines. Both men and women suffer from this imperfection, although the majority of those who suffer from this skin condition are pregnant women. Stretch marks may occur on the breasts, the upper arms, the buttocks, thighs and across the entire abdomen. Stretch marks may appear in patients after a breast augmentation or other cosmetic surgery procedures.

Stretch marks are wide purplish red lines on the skin which appear on different areas of the body as the pregnancy develops with ever increasing stretching of the skin. Stretch marks are most noticeable in the beginning when they are raised, pink, reddish brown or dark brown lines that later turn to a brighter purplish or a brisk red. In the pregnancy context, hormonal changes help the skin and ligaments to relax and stretch. During the postpartum period, these red lines can turn to silver. They then gradually flatten and fade out to a less noticeable silvery color. Eventually they will become a few shades lighter than the natural skin tone.

One explanation for the formation of stretch marks is best explained through pregnancy related stretch marks. As the uterus becomes larger and the breasts develop, the skin in certain women is not able to keep up with this rapid growth. The fibrous and elastic tissue in the skin is damaged and stretch marks form. As the stretching process increases, more scar tissue is accumulated and the stretch marks increase in width.

Stretch marks are not a very well understood skin condition. There are some known factors that determine if one is susceptible to the condition of stretch marks. Stretch marks have been linked to genetics and some estimate that about 15 to 20 percent of the population is genetically "stretch mark free." Ethnicity also factors into whether one will develop stretch marks. Darker skinned people tend to get less stretch marks than fair-skinned people.

Some dermatologists have suggested that stretch marks are often mistakenly blamed on the rapid stretching of the skin associated with such life events as pregnancy and growth spurts. These dermatologists have stated that stretch marks are the result of an increased level of circulating glucocorticoids throughout the bloodstream. This hormone, secreted by the adrenal glands, becomes elevated during pregnancy, adolescence, with obesity, weight lifting and Cushing's disease.

These dermatologists speculate that the glucocorticoids responsible for the development of a stretch marks affect the dermis by preventing the fibroblasts from forming collagen and elastin fibers, necessary to keep rapidly growing skin taut. This creates a lack of supportive material, as the skin is stretched and leads to dermal tearing. The epidermal cells are also affected, so the epidermis becomes thin and flattened, allowing for more visibility of the defects below.

Striae are a disfiguring skin condition normally associated with obesity, pregnancy and adolescent growth and are a pathological symptom of Cushing's, Marfan's and Ehlers-Danlos syndrome syndromes, diabetes mellitus[6] and long term use of topical and systemic steroids. The pathogenesis of stretch marks is as yet unknown but is thought to be a response to minimal or excessive stretching of skin[1]. Previous histo-pathological analysis of stretch marks demonstrated loss of dermal papillae and epidermal changes including atrophy, loss of rete ridges and conflicting observations regarding collagen and elastic fibers. More recent studies indicate that steady-state mRNA levels of collagens, elastin and fibronectin are decreased. Studies aimed at quantifying protein levels of elastin and fibrillin in stretch marks further confirmed decreased levels of both.

In 1982 Pieraggi and co-workers proposed that stretch marks are perhaps a consequence of fibroblast dysfunction, based upon their histological observations that fibroblasts were globular, quiescent, and appeared to lose all signs of fibrillar secretion in stretch marked skin. This implies that perhaps dermal fibroblasts in stretch marks have, temporarily or permanently, impaired proliferative and synthetic capabilities with regard to extracellular matrix. Elastic fibers are perhaps the most under-studied extracellular matrix components in skin and potentially a key player in stretch mark formation as there is no strong evidence that collagen levels are affected.

Stretch marks may be induced by excessive mechanical stretching of skin to the point of rupturing dermal elastic fibers and that local fibroblasts are unable to adequately repair or replace these ECM components that are solely responsible for the resilience of skin. Since many patients with stretch marks do not display any obvious signs of known genetic diseases permanently affecting connective tissue, these lesions may develop as a consequence of acquired metabolic disturbances that significantly diminish the reparatory abilities of dermal fibroblasts.

A better understanding of the development of stretch marks is necessary. It is generally understood that stretch marked skin contains lower collagen and elastin content than normal/healthy skin, but a biological analysis of stretch marked skin could lead to the development of enhanced therapeutic treatments.

Not all women will develop stretch marks associated with pregnancy. There are some factors that women may control to reduce the chance of stretch marks. Dry skin tends to be less elastic than well nourished or oily skin. Thus, dryer skin tends to be more susceptible to stretch marks. Part of keeping skin healthy and well-hydrated is dietary. Healthy skin will stretch better and will also repair itself quickly with little damage. Rapid or excessive weight gain will only compound the problem of stretch marks and likely cause more.

Some commonly known preventative measures to reduce the appearance of stretch marks include the follow therapies: massaging skin with a glove or a massage brush to increase circulation; and eating foods that contribute to the overall health of your skin, such as those high in vitamins C and E, zinc and silica. Zinc is especially important because it is linked to cellular growth. Exercising regularly and slow and steady weight gain during pregnancy also may prevent the formation of stretch marks. Several active ingredients have been identified as beneficial to the prevention of stretch marks including emu oil and vitamin E oil. Vitamin A is also a good overall moisturizer, but not as effective as tretinoin, or Retin-A, which helps exfoliate the skin and form healthy new cells.

Several treatments are also known to reduce the appearance of stretch marks. Stretch marks may never entirely be diminished. The sooner one begins treating stretch marks, while they are still reddish or purple, the better likelihood of diminishing their appearance. Once they flatten down and become more silvery they are more difficult to treat. There are several treatments on today's market that range from all-natural creams to invasive surgical measures.

Natural creams and oils include for example, Vitamins A and E and emu oil, are all natural, non-invasive treatments. Retin acid cream or glycolic acid are also known, which act to slough off the top skin layers and stimulate the skin. Another promising new treatment that can help the reduction and prevention of stretch marks include microdermabrasion. In this procedure, a dermatologist administers a stream of fine, chemically inert crystals onto the skin to exfoliate the outer most layers of the epidermis. Laser therapies have also been used to eliminate the appearance of stretch marks. A tiny pulse is emitted from the laser and is absorbed by the blood vessels in the affected area below the skin. Blood vessels rupture, bruise and recover in an accelerated healing process. Reducing contact with the sun and keeping the skin soft and moist have been general suggestions for patients with stretch marked skin.

Finally, cosmetic surgery, which is usually used as a last resort, may be used for the most severe scarring from stretch marks. A tiny incision is made along the length of the stretch mark and the affected area is removed and then stitched together.

There remains a need to identify patients who have a high incidence of stretch marks. There remains a need to identify the causes of stretch marks and how the skin's biological content changes from normal to stretch marked skin. There remains a need to objectively identify the likelihood of the development of stretch marks. There also remains a need to develop treatments and protocols, which may stimulate elastogenesis and the production of the extracellular matrix components in damaged or stretch marked skin. Additionally, stretch marked skin may provide a basis for therapies relating to the stimulation of cellular proliferation and elastogenesis. The use of stretch marked skin which contains a loss of elastin fibers may be used to determine the effectiveness of several potential therapies which may generate or stimulate cellular function in the skin.

Aspects of the present invention delineate possible functional differences between dermal fibroblasts derived from biopsies of unaffected skin regions of patients with stretch marks and fibroblasts derived from skin of normal age-matched individuals. Aspects further provide methods for determining functional differences between fibroblasts derived from these two groups, thereby allowing for the prediction of individuals that may be predisposed for development of striae distensae in skin, challenged by otherwise physiological stretch during the pregnancy. Aspects of the invention provide preventive treatment(s) for individuals diagnosed with predisposition to stretch mark development and eventual treatment of fully developed lesions.

SUMMARY

Losing collagen and elastin in the skin causes stretch marks, loss of tone, fine lines and wrinkles. Stretch marked or otherwise damaged skin has lost some or all of its collagen and/or elastin content in addition to some or all of its ability to form collagen and/or elastin fibers. Several therapeutic compositions of the present invention are formulated to treat damaged or stretched marked skin. These therapeutic compositions comprise an elastin digest from proteolytic digestion of insoluble elastin derived from mammalian ligaments with a protein digesting composition. Additionally, several method embodiments of the present invention describe treatments for stretch marked or damaged skin. Another method of the present invention is a method for the prevention of stretch marks.

Various method embodiments of the present invention comprise assessing the biological state of dermal tissue of a patient. The biological state may be assessed by one or more tests comprising determining extracellular matrix protein content of the dermal tissue, obtaining fibroblasts derived from the dermal tissue, determining the potential of fibroblasts to synthesize an extracellular matrix protein, determining the DNA content of the fibroblasts, assessing kinetics of fibroblast outgrowth from fragments of the dermal tissue, determining cellular proliferation and migration rates of the fibroblasts, and assessing rates of extracellular matrix component production. From the assessed biological state of the dermal tissue, the regenerative potential of dermal tissue in a patient may be determined. Additionally, from the assessed biological state of the dermal tissue of a patient, the likelihood of developing dermal stretch marks in a patient may be determined. In a further embodiment the dermal tissue is obtained from a skin biopsy to assess the biological state of dermal tissue.

One embodiment of the present invention is a method of diagnosing the potential to develop stretch marks. The diagnostic test comprises determining extracellular matrix protein content of the dermal tissue, obtaining fibroblasts derived from the dermal tissue, determining the potential of fibroblasts to synthesize an extracellular matrix protein, determining the DNA content of the fibroblasts, assessing kinetics of fibroblast outgrowth from fragments of the dermal tissue, determining cellular proliferation and migration rates of the fibroblasts, and assessing rates of extracellular matrix component production. Patients identified as likely candidates to develop stretch marks may then be given therapeutic treatments to prevent the formation of stretch marks. Through the analysis of a series of dermal tissue samples over time, a method of monitoring the aging process of the dermal tissue of a patient is possible.

An aspect of the invention provides a method of monitoring the aging process comprising determining extracellular matrix protein content of the dermal tissue, obtaining fibroblasts derived from the dermal tissue, determining the potential of fibroblasts to synthesize an extracellular matrix protein, determining the DNA content of the fibroblasts, assessing kinetics of fibroblast outgrowth from fragments of the dermal tissue, determining cellular proliferation and migration rates of the fibroblasts, and assessing rates of extracellular matrix component production.

Another embodiment of the invention is a diagnostic test to determine the regenerative potential of a dermal tissue sample from a patient. The test comprises determining extracellular matrix protein content of the dermal tissue, obtaining fibroblasts derived from the dermal tissue, determining the potential of fibroblasts to synthesize an extracellular matrix protein, determining the DNA content of the fibroblasts, assessing kinetics of fibroblast outgrowth from fragments of the dermal tissue, determining cellular proliferation and migration rates of the fibroblasts, and assessing rates of extracellular matrix component production.

Another embodiment of the invention is a method of determining whether a therapeutic composition should be administered to a patient to treat the dermal tissue. This method comprises determining extracellular matrix protein content of the dermal tissue, obtaining fibroblasts derived from the dermal tissue, determining the potential of fibroblasts to synthesize an extracellular matrix protein, determining the DNA content of the fibroblasts, assessing kinetics of fibroblast outgrowth from fragments of the dermal tissue, determining cellular proliferation and migration rates of the fibroblasts, and assessing rates of extracellular matrix component production.

Aspects of the invention further provide a method of treating stretch marked dermal tissue comprising administering to a site of stretch marked dermal tissue of a patient an effective amount of a composition comprising an elastin digest derived from proteolytic digestion of elastin derived from a mammal with a protein digesting composition. Another embodiment provides an effective amount of at least one of an elastin peptide fragment, a manganese salt, a trivalent iron component, or a polyphenolic compound, or derivative thereof. The elastin peptide fragment may have the formula $X_1GX_2X_3PG$ wherein $X_1$ is the amino acid V or I; $X_2$ is the amino acid A, L or V; and $X_3$ is the amino acid M, S, or A. In another embodiment the manganese salt component is chosen from the group of manganese salt of L-Pyrrolidone Carboxylic Acid, manganese chloride, manganese ascorbate, manganese gluconate and manganese sulfates. The trivalent iron component may be ferric ammonium chloride. In an embodiment the polyphenolic compound can be tannic acid or ellagic acid. In a further embodiment the composition stimulates cell migration in the tissue to which it is administered. The composition may further stimulate cell proliferation in the tissue to which it is administered. An embodiment wherein the composition stimulates the endogenous synthesis and deposition of elastin in the tissue to which it is administered is also provided.

Embodiments of the invention further provide a method of preventing the appearance of stretch marks on dermal tissue comprising administering to a site on dermal tissue of a patient an effective amount of a composition comprising an elastin digest derived from proteolytic digestion of elastin derived from a mammal with a protein digesting composition. A further embodiment comprises an effective amount of at least one of an elastin peptide fragment, a manganese salt, a trivalent iron component, or a polyphenolic compound, or derivative thereof.

Additionally, various therapeutic compositions to treat the dermal tissue of a patient are herein described. One aspect of the invention provides a therapeutic composition for the treatment of damaged skin comprising an elastin digest derived from proteolytic digestion of elastin derived from a mammal with a protein digesting composition. In a further embodiment the damaged skin is stretch marked skin. In another embodiment the damaged skin has lost substantial collagen and elastin fiber content. In one embodiment the therapeutic composition further comprises an effective amount of at least one of an elastin peptide fragment, a manganese salt, a trivalent iron component, or a polyphenolic compound, or derivative thereof. The elastin peptide fragment may have the formula $X_1GX_2X_3PG$ wherein $X_1$ is the amino acid V or I; $X_2$ is the amino acid A, L or V; and $X_3$ is the amino acid M, S, or A. In another embodiment the manganese salt component is chosen from the group of manganese salt of L-Pyrrolidone Carboxylic Acid, manganese chloride, manganese ascorbate, manganese gluconate and manganese sulfates. The trivalent iron component may be ferric ammonium chloride. In an embodiment of the therapeutic composition the polyphenolic compound can be tannic acid or ellagic acid.

A potential therapeutic composition may be tested on various fibroblasts to determine its effectiveness in stimulating the regenerative potential of the extracellular matrix components of the skin. Damaged or stretched marked skin may be used in the development of various diagnostic therapies relating to the inducement of the extracellular matrix components of the skin due to the loss of elastic fibers generally found in stretch marked skin.

DESCRIPTION OF DRAWINGS

The file of this patent contains at least one photograph or drawing executed in color. Copies of this patent with color drawing(s) or photograph(s) will be provided by the Patent and Trademark Office upon request and payment of necessary fee.

For a fuller understanding of the nature and advantages of the present invention, reference should be had to the following detailed description taken in connection with the accompanying drawings, in which:

FIG. 3. (A) displays the results of metabolic labeling of cultured fibroblasts with radioactive valine, followed by biochemical assay of newly produced elastin in both normal fibroblasts and fibroblasts derived from stretch marked skin. (B) and (C) display the proliferation rates for both fibroblasts derived from the stretch marked skin and normal skin fibroblasts as measured by assay of total DNA (B) and incorporation of radioactive thymidine (C).

FIG. 4. (A) displays a comparison of the migration rates of normal skin fibroblasts to stretch marked skin fibroblasts when maintained in DMEM medium with 5% FBS. (B) displays the potential of a therapeutic formulation according to the present invention which stimulates migration of fibroblasts derived from both normal and stretch marked skin.

FIG. 5. Displays representative micrographs depicting histological sections of biopsy of normal skin taken from 40 year old women (A), biopsy taken from "healthy looking" skin region of 44 year old women with stretch marks (B) and biopsy of actual stretch mark lesion from 47 year old women (C). All section were stained with Movat's pentachrome, original magnification 20×.

FIG. 6. FIG. 6(A) displays the actual content of DNA (6A-1) and total protein (6A-2) measured from biopsies derived from normal looking skin of patients without stretch marks, with stretch marks and stretch marked skin. FIG. 6(B) displays the results of biochemical analysis demonstrating that biopsies derived from "normally looking" skin of patients with stretch marks contained an average 16% less-DNA (6B-1) and 36% less protein (6B-2) per 1 mg of their wet weight than biopsies obtained from skin of "normal" individuals. Biopsies derived from the actual stretch marks contain even more pronounced deficiency of total DNA and total protein as compared to normal skin tissues.

FIG. 7. FIG. 7A displays the actual amount of protein measured in biopsies from normal skin, normal skin with stretch marks and stretch marked skin. FIG. 7B displays the results of biochemical analysis demonstrating that biopsies derived from "normally looking" skin of patients with stretch marks contained an average 44% less NAOH-insoluble elastin per 1 µg DNA than biopsies obtained from skin of "normal" individuals. The level of insoluble elastin in biopsies from actual stretch marks did not exceeded 20% of values detected in normal skin biopsies.

FIG. 10A and FIG. 10B demonstrate that fibroblasts derived from normally-looking skin of patients with stretch marks, and fibroblasts from the stretch marked skin demonstrate slower proliferation rates as compared to fibroblasts derived from volunteers with no history of stretch marks.

FIG. 13. (A) Results of the quantitative analysis of [$^3$H]-valine labeled insoluble elastin detected in 7 day-old secondary cultures of biopsy-derived fibroblasts (passage 1) demonstrate that fibroblasts derived from normally-looking skin of patients with stretch marks produce much less insoluble elastin than normal fibroblasts and that fibroblast derived from the stretch marked skin deposit only traces of insoluble elastin. (B) In contrast, results of similar assay performed in passage 4 of biopsy derived fibroblasts demonstrate similar levels of metabolically labeled insoluble elastin in all experimental groups.

DETAILED DESCRIPTION

Figure 1:
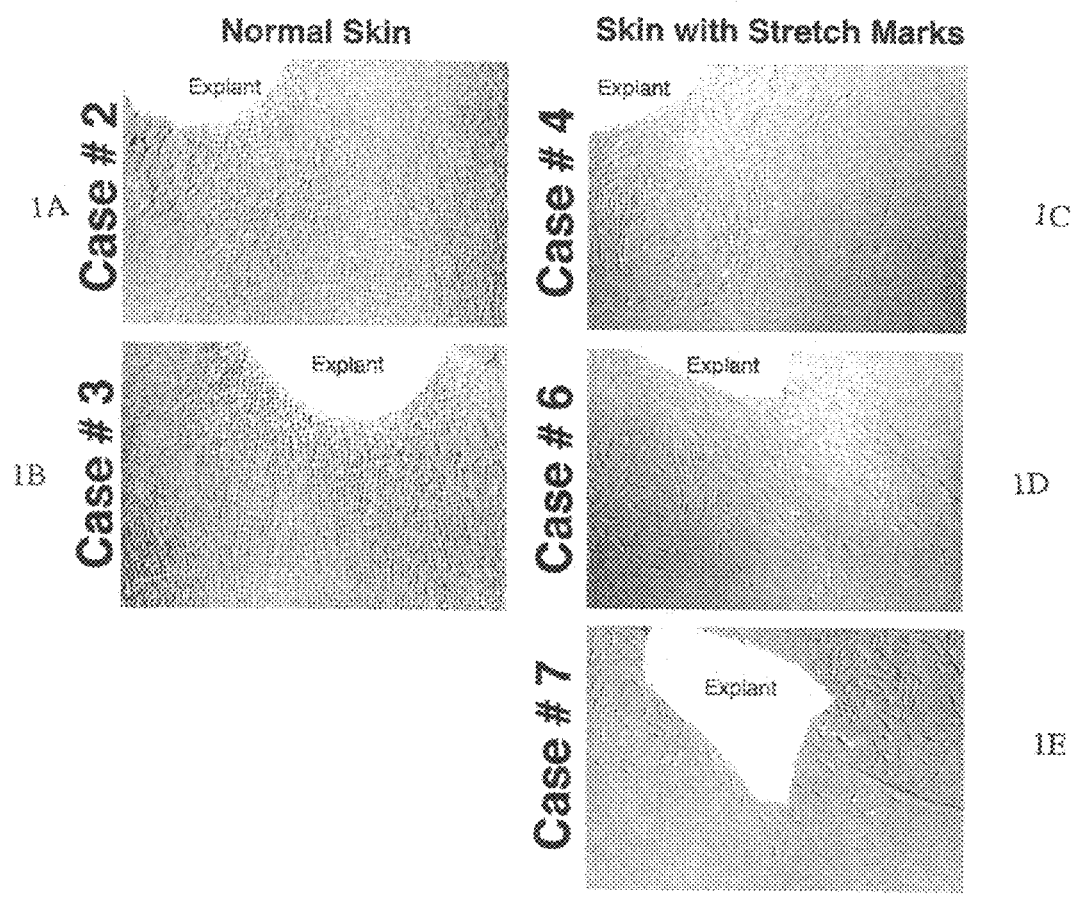
FIG. 1 compares the fibroblasts of explants of dermal tissue derived from skin biopsies of patients with stretch marks (FIG. 1A and FIG. 1B) with explants derived from normal skin patients (FIG. 1C, FIG. 1D and FIG. 1E).

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims.

It must also be noted that as used herein and in the appended claims, the singular forms "a", "an", and "the" include plural reference unless the context clearly dictates otherwise. Thus, for example, reference to an "fibroblast" is a reference to one or more fibroblasts and equivalents thereof known to those skilled in the art, and so forth. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

The methods as described herein for use contemplate prophylactic use as well as curative use in therapy of an existing condition. As used herein, the term "about" means plus or minus 10% of the numerical value of the number with which it is being used. Therefore, about 50% means in the range of 45%-55%.

"Administering" when used in conjunction with a therapeutic means to administer a therapeutic directly into or onto a target tissue or to administer a therapeutic to a patient whereby the therapeutic positively impacts the tissue to which it is targeted. Thus, as used herein, the term "administering", when used in conjunction with elastin digest, can include, but is not limited to, providing an elastin digest into or onto the target tissue; providing an elastin digest systemically to a patient by, e.g., intravenous injection whereby the therapeutic reaches the target tissue; providing an elastin digest in the form of the encoding sequence thereof to the target tissue (e.g., by so-called gene-therapy techniques). "Administering" a composition may be accomplished by injection, topical administration, or by either method in combination with other known techniques. Such combination techniques include heating, radiation and ultrasound.

The term "improves" is used to convey that the present invention changes either the appearance, form, characteristics and/or the physical attributes of the tissue to which it is being provided, applied or administered. The change in form may be demonstrated by any of the following alone or in combination: enhanced appearance of the skin; increased softness of the skin; increased turgor of the skin; increased texture of the skin; increased elasticity of the skin; decreased wrinkle formation and increased endogenous elastin production in the skin, increased firmness and resiliency of the skin.

The terms "mimetic," "peptide mimetic" and "peptidomimetic" are used interchangeably herein, and generally refer to a peptide, partial peptide or non-peptide molecule that mimics the tertiary binding structure or activity of a selected native peptide or protein functional domain (e.g., binding motif or active site). These peptide mimetics include recombinantly or chemically modified peptides, as well as non-peptide agents such as small molecule drug mimetics, as further described below.

Unless otherwise indicated, the term "skin" means that outer integument or covering of the body, consisting of the dermis and the epidermis and resting upon subcutaneous tissue.

As used herein, the term "therapeutic" means an agent utilized to treat, combat, ameliorate, prevent or improve an unwanted condition or disease of a patient. In part, embodiments of the present invention are directed to improve the functionality, the appearance, the elasticity, and/or the elastin content of damaged or stretch marked skin. As it applies to damaged or stretch marked skin, it is measured by elasticity, turgor, tone, appearance, degree of wrinkles, youthfulness, and diminished appearance of stretch marks.

A "therapeutically effective amount" or "effective amount" of a composition is a predetermined amount calculated to achieve the desired effect, i.e., to effectively promote improved tissue elasticity in damaged or stretch marked skin. A therapeutically effective amount of a therapeutic composition of this invention, for example, an elastin digest, is typically an amount such that when it is administered in a physiologically tolerable excipient composition, it is sufficient to achieve an effective local concentration in the tissue. Effective amounts of compounds of the present invention can be measured by improvements in tissue elasticity, endogenous elastin production, tissue function (elasticity), or tissue appearance and tone.

Generally speaking, the term "tissue" refers to any aggregation of similarly specialized cells which are united in the performance of a particular function. As used herein, "tissue", unless otherwise indicated, refers to tissue which includes elastin as part of its necessary structure and/or function. For example, connective tissue which is made up of, among other things, collagen fibrils and elastin fibrils satisfies the definition of "tissue" as used herein. Additionally, elastin appears to be involved in the proper function of blood vessels, veins, and arteries in their inherent visco-elasticity.

Damaged skin means skin that has lost substantial collagen and/or elastin content. Alternatively, damaged skin may mean that skin has substantially lost its ability to produce collagen and/or elastin. Stretch marked skin is skin that has lost substantial collagen and/or elastin content.

It has been found that an objective assessment of the actual biological state of the human skin and the prediction of its regenerative potential after exposure to certain stimulatory factors is possible according to the several embodiments of the present invention.

In one aspect of the present invention, a method of diagnosing the regenerative potential of dermal tissue in a patient is provided. Preferably, the method comprises establishing a baseline value for normal dermal tissue; obtaining a sample of dermal tissue from said patient; and comparing said sample of dermal tissue from the patient with the baseline value for normal dermal tissue to identify a quantitative difference between the sample and normal tissue. The quantitative difference may be reflected in a difference in a value selected from the group consisting of: the DNA content of the fibroblasts in said dermal tissue; the extracellular matrix protein content of said dermal tissue; the connective tissue content of said dermal tissue; collagen content of said dermal tissue; fibrillin content of said dermal tissue; the rate of proliferation of fibroblasts in said dermal tissue; the rate of migration of fibroblasts in said dermal tissue; the rate of connective tissue synthesis in said dermal tissue; the rate of extracellular matrix protein by said fibroblasts; and a combination thereof. In preferred embodiments, the quantitative difference may be reflected in a difference in a value of the DNA content of the fibroblasts in said dermal tissue and the extracellular matrix protein content of said dermal tissue. In another preferred embodiment, the quantitative difference may be reflected in a difference in a value of the rate of proliferation of fibroblasts in said dermal tissue and the rate of connective tissue synthesis in said dermal tissue. The sample of dermal tissue from the patient may be obtained from either stretch-marked skin or non-stretch-marked skin. The sample of dermal tissue from the patient may be obtained using a skin punch biopsy.

A method of diagnosing the potential for the development of stretch marks in a patient comprising: establishing a baseline value for normal dermal tissue; obtaining a sample of dermal tissue from said patient; and comparing said sample of dermal tissue from the patient with the baseline value for normal dermal tissue to identify a quantitative difference between the sample and normal tissue. The quantitative difference is reflected in a difference in a value selected from the group consisting of: the DNA content of the fibroblasts in said dermal tissue; determining the extracellular matrix protein content of said dermal tissue; the connective tissue content of said dermal tissue; collagen content of said dermal tissue; fibrillin content of said dermal tissue; the rate of proliferation of fibroblasts in said dermal tissue; determining the rate of migration of fibroblasts in said dermal tissue; the rate of connective tissue synthesis in said dermal tissue; the rate of extracellular matrix protein by said fibroblasts; and a combination thereof. In preferred embodiments, the quantitative difference is reflected in a difference in a value of the DNA content of the fibroblasts in said dermal tissue and the extracellular matrix protein content of said dermal tissue or the quantitative difference is reflected in a difference in a value of the rate of proliferation of fibroblasts in said dermal tissue and the rate of connective tissue synthesis in said dermal tissue.

In a further embodiment, a method of establishing a treatment protocol is provided. The method may comprising determining the likelihood of stretch marks forming; and pretreating the affected area to mitigate the occurrence of stretch marks. The likelihood of stretch marks being formed may be determined by comparing a sample of dermal tissue from a patient with a baseline value for normal dermal tissue to identify a quantitative difference between the sample and normal tissue, wherein the difference in a value selected from the group consisting of: the DNA content of the fibroblasts in said dermal tissue; the extracellular matrix protein content of said dermal tissue; the connective tissue content of said dermal tissue; the collagen content of said dermal tissue; the fibrillin content of said dermal tissue; determining the rate of proliferation of fibroblasts in said dermal tissue; the rate of migration of fibroblasts in said dermal tissue; the rate of connective tissue synthesis in said dermal tissue; the rate of extracellular matrix protein by said fibroblasts; and a combination thereof. The area may be pretreated with the therapeutic compositions of the present invention described further herein.

In a further embodiment, a kit is provided for determining the propensity for forming stretch marks. The kit may comprise components to measure a value selected from the group consisting of: the DNA content of the fibroblasts in said dermal tissue; the extracellular matrix protein content of said dermal tissue; the connective tissue content of said dermal tissue; collagen content of said dermal tissue; fibrillin content of said dermal tissue; the rate of proliferation of fibroblasts in said dermal tissue; the rate of migration of fibroblasts in said dermal tissue; the rate of connective tissue synthesis in said dermal tissue; the rate of extracellular matrix protein by said fibroblasts; and a combination thereof.

Several embodiments of the present invention make use of skin samples (dermal tissue) from patients. These skin samples may be collected in any suitable manner, such as by a biopsy. Several embodiments make use of a punch skin biopsy. One skilled in the art is generally familiar with the procedure and utility of a punch skin biopsy. A punch skin biopsy is a short procedure to remove a small piece of skin tissue for examination under a microscope. A punch skin biopsy is usually carried out to determine or confirm a diagnosis. A local anesthetic will be used to numb the biopsy site (i.e. a topical cream and injection). A skin punch biopsy needle is inserted into a patient's skin, rotated and a small circle of skin is carefully removed. The test has been used to identify cancers and benign growths, to help diagnose chronic bacterial and fungal skin infections, and to identify other skin conditions. However, the punch skin biopsy has not been used to identify skin that has lost existing elastic fibers or extracellular matrix components.

The use of a skin biopsy in which an evaluation of extracellular matrix content is determined may thus be used as a diagnostic in the prevention of the formation of wrinkles, permanent stretch marks, and other skin imperfections. A skin biopsy to determine extracellular content may be used to identify patients with damaged skin in order to provide therapeutic compositions to these patients targeted to stimulate the production of extracellular components and induce cellular proliferation. A diagnostic test may also be used to identify patients likely to develop stretch marks in order to provide these patients with a preventative treatment. Additionally, a skin biopsy to determine extracellular content may be used to provide a basis for the testing of numerous factors, which can potentially stimulate the production of extracellular components and induce cellular proliferation. Therefore prognostic or predictive assessment of extracellular functions may be made of patients according to several methods of the present invention.

Decrease in number of dermal fibroblasts, loss of an extracellular matrix (ECM) component, or metabolic dormancy of remaining fibroblasts that are unable to repair the skin damage induced by various intrinsic or extrinsic agents contribute to the aging of skin. Especially, loss of existing elastic fibers, and lack of cellular potential to replace this ECM component, which is solely responsible for dermal resilience, inevitably contributes to formation of wrinkles and permanent stretch marks.

Method embodiments of the present invention provide a reliable test allowing for the objective assessment of the actual biological state of the human skin and the prediction of its regenerative potential after exposure to certain stimulatory factors.

In the several testing embodiments of the present invention, assays of total protein and total DNA content in a skin biopsy may be determined, followed by histological morphometric calculation of the Cell/Matrix ratio. These evaluations provide valuable initial information about the stage of aging of the tested skin. More information about biological potential of dermal fibroblasts of a particular patient may be obtained after in vitro assessment of the kinetic of fibroblasts outgrowth from explants (fragments of the biopsy of about 0.1 mm in size), followed by assays of cellular proliferation and migration rates in secondary cultures.

Additionally, in the several testing embodiments of the present invention, biochemical and immunochemical assessment of the capability of fibroblasts to produce components of extracellular matrix, including collagens, fibrillin, fibronectin, proteoglycans and especially elastin, the most durable component of the ECM solely responsible for dermal resilience, may be also estimated after metabolic labeling of cultured cells and immunostaining with a panel of specific antibodies.

The second and third passages of fibroblasts derived from biopsies of patients with the damaged skin or those with a history of stretch marks may be used to test numerous factors that can potentially induce cellular proliferation and stimulate production of ECM components, such as elastin. With the use of multiple biopsies of patients over time, the rate of cellular proliferation may be determined for a particular patient. Thus the effect of therapeutic compositions on the proliferation rates and on elastogenesis may be better understood. Elastogenesis and induced proliferation of the ECM attributable to the therapeutic compositions may be compared to normal healthy cellular function.

An understanding of biological make-up, migration rates, elastogenesis rates, and proliferation rates in both normal/healthy and stretch marked skin allows for therapies to be developed and administered such that the combined effect of therapeutic stimulation and healthy cellular function are maximized. An understanding of the cellular make-up and function of both normal/healthy skin and stretch marked skin will allow for the monitoring of the aging of the skin.

As discussed above, the condition of stretch marks is not well understood. Some women will never develop stretch marks associated with pregnancy while many more will. Additionally, both men and women alike would benefit from a diagnostic test which predicts the likelihood of the development of stretch marks. As explained above, stretch marks may appear in both men and women and may occur as the result of rapid weight gain or loss, weight lifting, adolescence, and cosmetic surgery.

One embodiment of the present invention is a diagnostic test in which an objective analysis would indicate whether a patient may develop stretch marks. A biopsy of a patient may be compared to gathered biopsies of normal and stretch marked skin. Biopsies may be taken before, after and/or in the earlier stages of pregnancy, before cosmetic surgery, before a planned diet, and before embarking on a strength or conditioning exercise program. A therapeutic treatment may then be administered to such patient screened as likely to develop stretch marks in order to prevent the appearance of the stretch marks. An alternative embodiment of the present invention is a diagnostic test in which a patient's stretch mark status is evaluated or a diagnostic test in which a patient's response to treatment is evaluated. In such embodiments, fibroblasts may be obtained from a patient and compared to controls or previous fibroblast samples from the patient, to determine the state of elastogenesis in the patient.

Another embodiment of the present invention is a method of assessing the biological state of dermal tissue of a patient. Another embodiment of the present invention is a method of predicting the regenerative potential of dermal tissue in a patient comprising obtaining fibroblasts derived from a biopsy of a patient, subjecting the fibroblasts to one or more tests to determine the ability of fibroblasts to produce ECM components, and predicting the regenerative potential of the dermal tissue. Another embodiment of the present invention is a method of predicting the potential development of dermal stretch marks in a patient. Another embodiment of the present invention is a method of monitoring the aging process of the dermal tissue of a patient. Another embodiment of the present invention is a method of determining whether a therapeutic composition should be administered to a patient to treat the dermal tissue of a patient.

Therapeutic compositions of the present invention preferably exhibit elastogenic properties. For example, suitable therapeutic compositions include, elastin derived peptides, elastin binding peptides, such as an elastin binding sextapeptide, or peptide mimetic thereof, plant-derived peptides, manganese-based compounds, and iron based compounds. Therapeutic compositions may also exhibit elastin stabilizing properties. For example, suitable therapeutic compositions may include a polyphenolic compound, or derivative thereof, such as but not limited to tannic acid or ellagic acid.

One therapeutic composition of the present invention relates to the treatment of damaged skin comprising an elastin digest derived from proteolytic digestion of elastin derived from a mammal with a protein digesting composition.

One method of the present invention relates to treating stretch marked dermal tissue comprising administering to a site of stretch marked dermal tissue of a patient an effective amount of a composition comprising an elastin digest derived from proteolytic digestion of elastin derived from a mammal with a protein digesting composition. Another method of the present invention relates to preventing the appearance of stretch marks on dermal tissue comprising administering to a site on dermal tissue of a patient an effective amount of a composition comprising an elastin digest derived from proteolytic digestion of elastin derived from a mammal with a protein digesting composition.

U.S. patent application Ser. No. 10/778,253, filed on Feb. 13, 2004 entitled, "Elastin Digest Compositions and Methods Utilizing Same," herein incorporated by reference, describes various compositions for the therapeutic and/or cosmetic treatment of elastin comprising tissues. Preferably such compositions stimulate the endogenous production of elastin or appear to enhance the elasticity of the skin and provide an external supply of peptide precursors of elastin that penetrate into the tissue to which it is applied. The Application describes compositions comprising an elastin digest derived from proteolytic digestion of insoluble elastin derived from mammalian ligaments with a protein digesting composition. Such compositions and techniques may be used in the various methods as described herein to treat stretch marked or otherwise damaged or aged skin.

For example, suitable compositions according to U.S. patent application Ser. No. 10/778,253 include, commercially available, Elastin E91 preparation from Protein Preparations, Inc., St. Louis, Mo., is a suitable elastin product to subject to digestion, having about 1,000 to 60,000 dalton molecular weight. Additionally, a series of digests available under the trade name ProK, and specifically ProK60, are elastin peptide mixture derived from the proteolytic digestion of insoluble Elastin derived from bovine neck ligaments, commercially available from Human Matrix Sciences, LLC. The digestion is accomplished with Proteinase K enzyme. The commercially available products will be referred to as E91 and ProK respectively and may be employed in the present therapeutic treatments described herein relating to stretch marked skin.

The term as used herein, "elastin digest" refers to any insoluble elastin derived from mammalian tissue or previously solubilized elastin (either chemically or enzymatically) that is proteolytically digested with a protein digesting composition. As described in the U.S. application Ser. No. 10/778,253, an elastin digest is a mixture of peptides. Additionally, the elastin digest of the present invention may comprise other epitopes for extracellular matrix proteins, cytokines, growth factors, and di-peptides.

Embodiments of the present invention relate to compositions comprising an elastin peptide which improves the appearance, the elasticity, and/or the elastin content of damaged or stretch marked skin. The compositions containing the elastin of the present invention may induce the synthesis of fibrillin and collagen in cell cultures. Additionally, the compositions may induce elastogenesis and/or migration in cells derived from subjects of different ages.

Suitable elastin digests may be obtained from proteolytic digestion, with a protein digesting composition, of insoluble elastin derived from connective mammalian tissues or ligaments, bovine neck ligaments in particular. Suitable protein digesting compositions, include for example, human elastase enzyme, Proteinase K enzyme, and thermolysin.

One therapeutic composition of the present invention relates to the treatment of damaged skin comprising plant-derived elastogenic peptides. One method of the present invention relates to treating stretch marked dermal tissue comprising administering to a site of stretch marked dermal tissue of a patient an effective amount of a composition comprising a plant derived peptide. Another method of the present invention relates to preventing the appearance of stretch marks on dermal tissue comprising administering to a site on dermal tissue of a patient an effective amount of a composition comprising a plant derived peptide.

U.S. Provisional Patent Application Ser. No. 60/671,557 entitled "Plant-Derived Elastin Binding Protein Ligands and Methods of Using the Same" filed Apr. 15, 2005, herein incorporated by reference in its entirety, discloses peptides, or peptide mimetics thereof, comprising the formula $X_1GX_2X_3PG$ wherein $X_1$ is the amino acid V or I; $X_2$ is the amino acid A, L or V; and $X_3$ is the amino acid M, S, or A may be provided, which bind to the elastin receptor on cells and stimulate the endogenous production of elastin-enriched ECM. The sextapeptide may be supplemented with one or more additional linking amino acid residues, for example the linking amino acid residues may comprise alanine residues, or analogues thereof. The linking amino acid residues link two sextapeptides, or peptide mimetics thereof, generating a sextapeptide dimer. In one embodiment, the two sextapeptides, or peptide mimetics thereof, within a linked sextapeptide dimer may be identical. In another embodiment the two sextapeptides, or peptide mimetics thereof, within a linked sextapeptide dimer may be different. In one embodiment the number of linking residues linking two sextapeptides, or peptide mimetics thereof, may be in the range of about 3-7, more preferably in the range from about 4-5.

The elastin peptide fragment components in the therapeutic formulation is typically present in amount from about 0.0002 to about 90% by weight of the formulation. These formulations may be employed directly as a constituent of therapeutic treatment, such as emulsions, lotions, sprays, ointments, creams and foam masks. Final products may contain up to 10% by weight but preferably 0.001 to 5% of such a solution though of course more concentrated or more dilute solutions may also be used in greater or lesser amounts. For example, an eye cream may comprise about 0.1% (w/w) and a facial cream may comprise about 0.025% (w/w) of a soluble elastin peptide fragment component in an excipient. Facial cream compositions usually comprise salts. Specifically, the elastin peptide fragment component of the present invention exists in cosmetic or therapeutic compositions at concentrations of about 10-1000 μg/ml, preferably about 25 μg/ml.

In a further embodiment, the therapeutic composition and methods herein may contain a manganese or iron based compound. U.S. patent application Ser. No. 11/062,377 entitled "Compositions for Elastogenesis and Connective Tissue Treatment" filed Feb. 22, 2005, herein incorporated by reference in its entirety discloses iron components, preferably trivalent iron components, such as, but not limited to, ferric ammonium chloride (FAC), which appear to stimulate new elastogenesis and the final extracellular deposition of elastin fibers and assists in the treatment of elastic tissue defects. The trivalent iron, when included in the composition, is generally present in an amount from about 5 to 20 weight percent. In one embodiment the trivalent iron component is generally present in an amount from about 0.01 to 5 weight percent, preferably from about 0.02 to 3 weight percent, and more preferably from about 0.03 to 2 weight percent of the composition. Typical concentrations of a trivalent iron, or salts thereof, component range from about 2-75 μM, or preferably from about 2-50 μM, most preferably from about 2-25 μM.

U.S. patent application Ser. No. 11/062,377 also describes suitable manganese salts that may be used in such therapeutics, including, but not limited to, manganese-PCA, manganese chloride, manganese ascorbate, manganese gluconate and manganese sulfates. Manganese-PCA ("Mn-PCA") is the manganese salt of L-Pyrrolidone Carboxylic Acid ("L-PCA"). The manganese salts in the formulation may be from about 0.0002% to about 90% by weight of the formulation. These formulations may be employed directly as a constituent of the composition, or may be applied as a separate composition, as emulsions, lotions, sprays, ointments, creams and foam masks. Final products may contain up to 10% by weight but preferably 0.001 to 5% of such active ingredient, though of course more concentrated or more dilute solutions may also be used in greater or lesser amounts. Specifically, the one or more manganese salt of the present invention exists in cosmetic or therapeutic compositions at concentrations of about 0.5-25 μM, preferably about 1.0 μM.

In a further embodiment, an abrasive composition may be utilized in the methods and compositions described herein. U.S. Provisional Application Ser. No. 60/684,500, entitled "Methods and Compositions for Improving the Appearance of Skin" and filed May 25, 2005, herein incorporated by reference in its entirety, describes various abrasive compositions containing therapeutic compositions, including elastogenic compounds. The abrasion of the upper most layer will remove the unwanted tissue of the damaged area of skin and allow for an enhanced penetration of a therapeutic compound of the invention and stimulate reconstruction and remodeling of the epidermis and dermis. Such compositions and techniques may be applied to reduce the incidence and prevalence of dermal stretch marks.

Other therapeutic compounds useful in the present invention include polyphenolic compounds, such as ellagic acid and tannic acid. U.S. Provisional Patent Application No. 60/665,966 entitled "Elastin Protective Polyphenolics" filed Mar. 29, 2005 discloses polyphenolic compounds or derivatives thereof, such as ellagic acid (EA) or tannic acid (TA), which appear to enhance net deposition of elastic fibers by dermal fibroblasts. The polyphenolic compounds, such as tannic acid and/or ellagic acid, may be present in an amount from about 0.01 to 80 weight percent, preferably from about 0.1 to 20 weight percent, and more preferably from about 0.5 to 10 weight percent. Typical concentrations of the polyphenolic compound, or derivative thereof, range from about 0.5 µgrams/ml to about 2.0 µgrams/ml, or more preferably from about 0.75 µgrams/ml to about 1.5 µgrams/ml, or more preferably about 1.0 µgrams/ml.

Therapeutic compositions of the present invention may also include various other active ingredients, additives, carriers, and excipients, of which are generally known in the art. Additionally, therapeutic compositions may contain ingredients that have generally been used in skin formulations.

The therapeutic compositions of the present invention may be formulated into any suitable preparation including gels, creams and lotions. Additionally, in another embodiment of the invention, compositions comprising an elastin digest may contain chemical preservatives, such as cetylpyridinium chloride, K-Sorbate, Na-Benzoate, various parabens, and/or other chemical preservatives. Other suitable additives in the therapeutic compositions of the present invention include sodium compounds and copper based compounds. Compounds comprising sodium are suitable additives for therapeutic compositions of the present invention. Sodium has been linked to stimulate elastogenesis. Compounds comprising copper are another suitable additives in the therapeutic compositions of the present invention.

Optionally, a sodium component, or pharmaceutically acceptable salt thereof, may also be included in a therapeutic composition of the invention. The sodium component is generally present in about 5 to 20 percent of the complex. The sodium component may generally be present in an amount of about 1 to 10 percent weight percent, or from about 5 to 7 percent weight of the composition.

A copper component may also be included in the therapeutic composition, and may be any copper compound or pharmaceutically acceptable salt thereof. The copper component inhibits elastase and assists in the treatment of elastic tissue defects. The copper compound may be in the form of copper sebacate. When included in a composition the copper component is generally present in an amount of about 5 to 20 weight percent of the copper compound, such as copper sebacate. The copper component is generally present in an amount of about 0.01 to 5 percent weight or from about 0.03 to 2 percent weight of the composition.

The dosage ranges for the administering of therapeutic composition of the invention are those large enough to produce the desired effect in which the condition to be treated is ameliorated. The dosage should not be so large as to cause adverse side effects. Generally, the dosage will vary with the age, condition, and sex of the patient, and the extent of damage of the dermal tissue in the patient, and can be determined by one of skill in the art.

A therapeutic composition may be administered parenterally by injection or by gradual infusion over time. For example, a therapeutic composition may be administered topically, locally, perilesionally, perineuronally, intracranially, intravenously, intrathecally, intramuscularly, subcutaneously, intracavity, transdermally, dermally, or via an implanted device, and they may also be delivered by peristaltic means. Although local topical delivery is desirable, there are other means of delivery, for example: oral, parenteral, aerosol, intramuscular, subcutaneous, transcutaneous, intamedullary, intrathecal, intraventricular, intravenous, intraperitoneal, or intranasal administration. The diffusion of the one or more peptides of the digest composition into the tissue may be facilitated by application of external heat or soaking of skin in a heated solution comprising an effective amount of the composition.

The several methods of testing fibroblasts to determined biological content and function of the dermal samples are described below. Fibroblasts may be treated and cultured in any known manner. For example, fibroblasts of the present examples were originally isolated by digestion of skin biopsies with mixture of 0.25% collagenase type I (Sigma) and 0.05% DNAse type 1 (Sigma) and then passaged by trypsinization and maintained in alpha-minimum essential medium supplemented with 20 mM Hepes, 1% antibiotics/antimycotics, 1% L-Glutamate and 5% fetal bovine serum (FBS). In some experiments, consecutive passages were tested. In some experiments the serum free medium was also used.

Metabolic labeling of cultured fibroblasts with [$^3$H]-valine may be used to assess the production of newly deposited insoluble elastin. This assay may be used to determine if stimulation of the deposition of cross-linked insoluble elastin has occurred in the culture. Elastogenic effects visible by biochemical assay may be confirmed by immunostaining with specific anti-elastin antibody.

Cell proliferation may be assessed by incorporated of [$^3$H]-thymidine into the DNA of fibroblasts. This test may also be used to determine if a potential therapeutic has mitogenic activity and stimulatory effects on cellular proliferation. The proliferation effect of a therapeutic may also be confirmed by an assay of total DNA content and by immunochemical detection or proliferation antigen Ki67.

Deposition of extracellular matrix components by the fibroblasts may be determined using known methods. For example, morphometric analysis may be used wherein cultures are immunstained with antibodies recognizing components of extracellular matrix.

Examples of the invention, described below, show biochemical assays of skin biopsies from actual stretch marks which demonstrated a striking decrease in DNA, total protein and elastin contents as compared with normal skin samples. The outgrowth of fibroblasts from explants of these biopsies taken directly from stretch marks was initially non-existent, and required at least 2-3 weeks of culture in medium with 10% serum to yield the first wave of outgrowing fibroblasts. These fibroblasts, maintained in secondary cultures, produced small amounts of collagen I and fibrillin-1 but did not deposit elastin. Since parallel biochemical tests of biopsies derived from healthy looking skin of patients with stretch marks and analysis of their cultured fibroblasts also demonstrated a significant decline in their proliferative, migrative and synthetic abilities, the skin of patients with stretch marks may contain a functionally impaired fibroblast phenotype that could be detected in cutaneous regions never having been challenged by physical forces.

The persistent local mechanical forces that are incurred during stretching of skin (for example, during pregnancy) may induce local stretch dependent lesions only in the presence of general metabolic deficiencies that harm the proper production or/and maintenance of dermal elastic fibers that are solely responsible for skin resiliency. The finding that the impaired fibroblast phenotype was reversible after prolonged exposure to normal fetal bovine serum, seems to suggest that the detected phenotype is not caused by a genetic defect but rather it may develop in response to a deficiency of certain humoral factor(s) lacking in serum of affected individuals.

Aspects of the invention provide in vitro tests that indicate that fibroblasts derived from "healthy-looking" regions of skin of patients with stretch marks are metabolically affected and functionally dormant. This suggests that stretch marks develop only in certain individuals whose genetic profile or actual metabolic status is compromised and thereby lead to functional dormancy of dermal fibroblasts, diminishing their potential for proper response to persisted mechanical stretching and fast repair of damaged ECM.

Thus, the described methods involving early passages of biopsy-derived dermal fibroblasts may constitute a useful diagnostic tool allowing for prediction whether a particular patient would develop stretch marks during pregnancy or substantial weight gain.

Moreover, the data provided by the Examples indicate that metabolically dormant fibroblasts, even those derived from actual stretch marks, can eventually recover their ability to produce new elastic fibers and proliferate, when maintained in the presence of normal serum. Thus, patients with the potential to develop stretch marks or patients with stretch marks will benefit by the compositions provided herein which can stimulate the proliferation and migration of fibroblasts into an area of a tissue and further stimulate fibroblast elastogenesis. Further embodiments provide for compositions that can stabilize the insoluble elastin polymers and protect them from proteolytic degradation, therein enhancing the increased deposition of elastin.

Aspects of the invention provide methods for determining a predisposition to develop stretch marks. Many patients have the potential to develop stretch marks, which may be reflected by acquired metabolic disturbances that notably, but not irreversibly, diminish the functional abilities of dermal fibroblasts for local tissue repair. Thus, identification of the metabolically impaired but "curable" fibroblasts opens a new avenue for development of a preventive treatment aimed at "awakening of lazy fibroblasts" in individuals diagnosed with predisposition to stretch mark development and eventual treatment of fully developed lesions.

The methods of the invention allow for the assessment of a biological state of a skin biopsy and the potential to develop dermal stretch marks. Aspects of the invention further provide methods to diagnose the regenerative potential of dermal tissue and to monitor the aging process. Compositions provided herein can be used to treat, prevent and restore dermal elasticity and normal tissue histology.

The following methods are used to illustrate the various embodiments of the present invention. The methods are exemplary methods and are not meant to limit the invention.

Punch biopsies were taken from "healthy" skin regions of 10 female patients, 24 to 47 year old, with stretch marks and from skin of 3 "normal" age-matched individuals. Additional biopsies were also taken from the stretch marked skin of 3 patients.

Histopathology. The distribution of extracellular matrix components in 4 μm thick histological sections were studied from each obtained skin biopsy. All histological sections were stained with Movat's pentachrome which shows elastin as black, glycosaminoglycans as green, collagen as yellow, smooth muscle as red and nuclei as dark blue. Previous studies have confirmed that the distribution of black-stained material with Movat's method entirely overlaps with immunodetectable elastin.

Biochemical analyses of the skin biopsies. The contents of total DNA was analyzed using the DNeasy Tissue System from Qiagen, and the total protein levels were assessed with the Bio-Rad protein assay Dye Reagent (Bio-Rad Laboratories), according the manufacturers instructions. The obtained values were than normalized per 1 mg of wet weigh of the tested samples. The content of insoluble elastin in the biopsies was assessed after 1 $mm^2$ tissue samples were weighted and boiled in 0.5 mL of 0.1N NaOH for 45 minutes to solubilize all matrix components except elastin. The resulting pellets containing the insoluble elastin were then solubilized in 200 μL of 0.25M hot oxalic acid for 1 hour and the protein content was assessed with Bio-Rad protein assay Dye Reagent kit. The results were normalized per DNA content of the same biopsy.

Cell cultures. Multiple fragments of the each obtained biopsy (explants) were first placed in culture dishes and maintained in alpha-minimum essential medium supplemented with 20 mM Hepes, 1% antibiotics/antimycotics, 10% fetal bovine serum (FBS) and 1% L-Glutamate for the initial outgrowth of skin fibroblasts. Fibroblasts growing out of all primary explants were detached by trypsinization, maintained in secondary cultures and analyzed through their four consecutive passages. Cell proliferation was assessed by incorporation of [$^3$H]-thymidine and production of the major components of extracellular matrix, elastin, fibrillin 1, fibronectin and collagen I were assessed by immunohistochemistry. The production of new elastin was also assessed after metabolic labeling of cultured fibroblasts with radioactive valine.

Migration from the initial explants. The migratory abilities of dermal fibroblasts present in the skin biopsies were assessed initially by observation of their initial outgrowth from the multiple small explants (1 $mm^2$) placed in the tissue culture dishes. The explants were observed by inverted microscopy with Nomarski-optic and images were collected daily for the consecutive 21 days. Images of each sample were captured and the number of migrating cells detected in the 25 $mm^2$ squares surrounding each explants were counted using Image-Pro Plus software. Fife explants derived from the single biopsy were analyzed.

Migration into scratch-gaps of monolayer secondary cultures. Fibroblasts obtained by trypsinization of the initial hallo of the primary explants (passage one) were plated on 30 mm culture dishes and incubated in medium supplemented with 10% FBS for 6 days until fully confluent at which time a 5 mm scratch-gap was introduced using a rubber policeman as previously described. Cultures were then incubated in media supplemented with 5% FBS for 7 days during which time their migration into the gaps was monitored using an inverted microscope. Five microscopic (2 $mm^2$) fields in each scratch-gap injury were evaluated under inverted microscope. Images of each sample were captured and the number of migrating cells into each field were counted using Image-Pro Plus program.

Cell Proliferation Assays. The fibroblasts derived from skin biopsies of normal individuals and from biopsies of normally looking skin of patients with stretch marks were suspended in alpha-MEM containing 5% FBS and initially plated in 6 well dishes at a density of 50 000/cells per well. The medium was changed 24 hours later, and parallel cultures were maintained for the next 48 hours. The cell density was then roughly estimated in each culture under the inverted microscope with Nomarski optics and then cells were trypsynized and counted in a haemocytometer. Parallel sextoplicate cultures incubated as above were also exposed to [$^3$H]-thymidine (2 µCi/well) for the last 24 hours. These cultures were then washed in PBS and treated with cold trichloroacetic acid (TCA) twice for 10 minutes at 4° C. Then, 0.5 ml of 0.3N NaOH was added to all dishes for 30 minutes and subsequently 200 µl aliquots of each culture were mixed with scintillation fluid and counted.

Immunocytochemistry. Ten-day-old cultures of fibroblasts derived from all skin biopsies, containing abundant extracellular matrix, fixed in cold 100% methanol, were incubated for one hour with 20 µg/ml of polyclonal antibody to tropoelastin (Elastin Products), with 20 µg/ml of polyclonal antibody to fibrillin 1 (Chemicon), with 2/g/ml of monoclonal antibody to fibronectin (Sigma) and with 10 µg/ml of polyclonal antibody to collagen type I (Chemicon). All cultures were then incubated with appropriate fluorescein-conjugated secondary antibodies (GAR-FITC or GAM-FITC) for an additional hour. Nuclei were counterstained with propidium iodide. Morphometric analysis of all cultures immunostained with individual antibodies recognizing extracellular matrix components was performed using an Olympus AH-3 microscope attached to a CCD camera (Optronix) and a computerized video analysis system (Image-Pro Plus software 3.0 for Macintosh, Media Cybernetics, Silver Spring, Md.).

Metabolic labeling and quantification of newly deposited insoluble elastin. Fibroblasts derived from biopsies of normal individuals and from normally looking skin of patients with stretch marks were grown to confluency in 30 mm cell culture dishes in quadruplicates. Three days latter 20 µCi of [$^3$H]-valine was added to each dish along with fresh media. Cultures were then incubated for another 72 hours and soluble and insoluble elastin were assessed separately in each culture. At the end of each experiment, media were removed and cell layers containing deposited extracellular matrix were then scraped in 0.1N NaOH, sedimented by centrifugation, and boiled in 0.5 mL of 0.1N NaOH for 45 minutes to solubilize all matrix components except elastin. The resulting pellets containing the insoluble elastin were then solubilized by boiling in 200 µL of 5.7 N HCl for 1 hour and the aliquots were mixed with scintillation fluid and counted. Final results reflecting amounts of metabolically labeled, insoluble elastin were expressed as CPM/µg DNA. DNA was determined with the DNeasy Tissue System from Qiagen.

Statistical Analysis. Differences between groups were analyzed with one-way analysis of variance (ANOVA). If analysis of variance demonstrated significant differences between groups, individual differences were analyzed with a two-tailed unpaired t test.

EXAMPLE 1

FIG. 1 compares the fibroblasts of explants of dermal tissue derived from skin biopsies of patients with stretch marks (1C, 1D, 1E) with explants derived from normal skin patients (1A, 1B). The first column represents dermal tissue derived from two patients with normal skin, which demonstrate an abundant migration of their fibroblasts to a site of explant (1A, 1B). By contrast, explants of dermal tissue derived from skin biopsies of patients with stretch marked skin, as seen in the three cases in the second column of FIG. 1 demonstrate very slow outgrowth of their fibroblasts. (1C, 1D, 1E). The cultures in FIG. 1 are 14-day-old cultures of small fragments (explants) of dermal biopsies derived from females with normal skin and with stretch marked skin.

EXAMPLE 2

Figure 2:
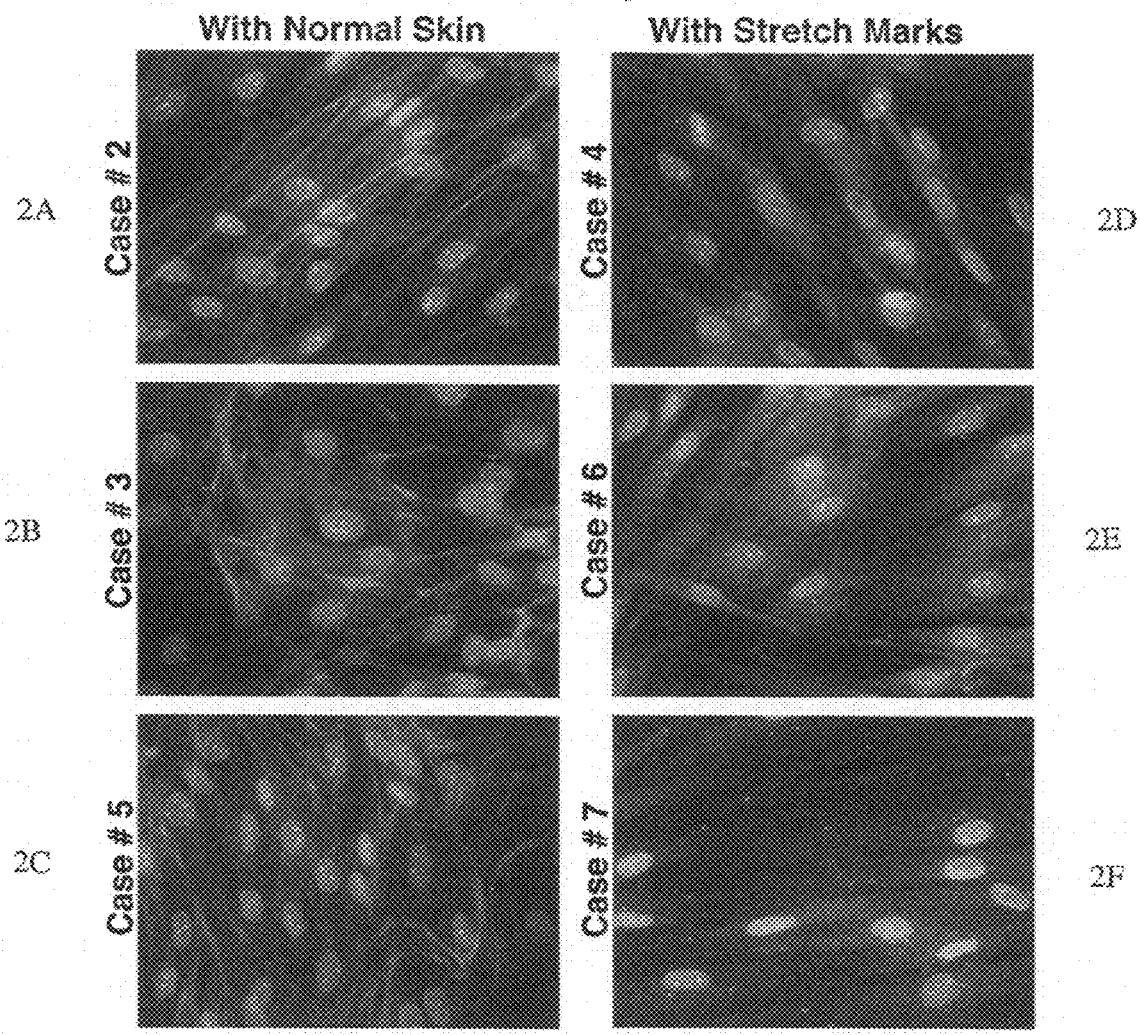
FIG. 2 displays the immunostaining of 7-day-old cultures which indicate that fibroblasts derived from patients with stretch marks (FIG. 2D, FIG. 2E and FIG. 2F) do not demonstrate any immuno-detectable elastin as compared to fibroblasts from normal skin (FIG. 2A, FIG. 2B and FIG. 2C).

FIG. 2 displays the immunostaining of 7-day-old cultures which indicate that fibroblasts derived from patients with stretch marks (2D, 2E, 2F) do not demonstrate any immuno-detectable elastin as compared to fibroblasts from normal skin (2A, 2B, 2C). FIG. 2 shows the production of elastic fibers in primary cultures of dermal fibroblasts derived from skin biopsies of females with normal skin (2A, 2B, 2C) and females with stretch marked skin (2D, 2E, 2F). Immunostaining was conducted with a specific anti-elastin antibody. In contrast to fibroblasts from normal skin (2A, 2B, 2C), which produce abundant elastic fibers, cultures of fibroblasts derived from patients with stretch marks (2D, 2E, 2F) do not demonstrate any immuno-detectable elastin production.

EXAMPLE 3

FIG. 3A displays the results of metabolic labeling of cultured fibroblasts with radioactive valine, followed by biochemical assay of newly produced elastin in both normal fibroblasts and fibroblasts derived from stretch marked skin. This test reveals the deposition of insoluble elastin in 7-day-old primary cultures of dermal fibroblasts by the incorporation of [$^3$H]-valine. Results confirm that fibroblasts derived from the stretch marked skin produce much less insoluble elastin than normal fibroblasts. The normal skin cultures tested deposited as much as about 11,000 cpm/dish as compared to about stretch marked skin which deposited only about 3,000 cpm/dish.

FIG. 3B displays the proliferation rates for both fibroblasts derived from the stretch marked skin and normal skin fibroblasts as measured by assay of total DNA and incorporation of radioactive thymidine (FIG. 3C). These results confirm that fibroblasts derived from the stretch marked skin show much lower proliferation rates than their counterparts derived from normal skin patients.

EXAMPLE 4

FIG. 4A displays a comparison of the migration rates of normal skin fibroblasts to stretch marked skin fibroblasts when maintained in DMEM medium with 5% FBS. In contrast to normal skin fibroblasts demonstrating vigorous migration into the scratch gap created in secondary cultures, fibroblasts derived from the stretch marked skin do not migrate, or migrated at a much slower rate.

FIG. 4B displays the potential of a therapeutic formulation according to the present invention which stimulates migration of fibroblasts derived from both normal and stretch marked skin. Addition of 25 µg/ml of ProK-60, an elastin digest available from Human Matrix Sciences LLC, into the culture medium proportionally stimulated migration of fibroblasts derived from both normal and stretch marked skin.

EXAMPLE 5

Histological analysis of skin biopsies taken from "normal looking" skin regions of 10 women with stretch marks revealed the existence of peculiar ECM. In all 10 analyzed cases this matrix was more compact than that of normal individuals but contained fewer elastic fibers that were thinner and often fragmented (FIGS. 5 A and B). Moreover the distribution of elastic fibers were uneven and in 7 out of 10 analyzed cases, the deficiency in elastic fiber content in the sub-epidermal zones was really striking and resembled those samples obtained from the actual stretch mark sites (FIG. 5). The latter were further characterized by a striking deficiency of collagen bundles, increased levels of proteoglycans, very thin epidermis and a visible loss of dermal papillae (FIG. 5C).

Biochemical analysis of biopsies derived from "normally looking" skin of patients with stretch marks contained an average 16% less-DNA (FIG. 6B-1) and 36% less protein per 1 mg of their wet weight (FIG. 6B-2) than biopsies obtained from skin of "normal" individuals (FIG. 6). They also contained an average 44% less NaOH-insoluble elastin per 1 μg DNA (FIG. 7B). The contents of total DNA (FIG. 6A-1, B-1) and total protein (FIG. 6A-2, B-2) in biopsies from the actual stretch marked skin demonstrated even more pronounced deficiencies as compared to normal skin (−55%, −64% respectively). Their level of insoluble elastin did not exceeded 20% of values detected in normal skin biopsies (FIG. 7B).

Figure 8:
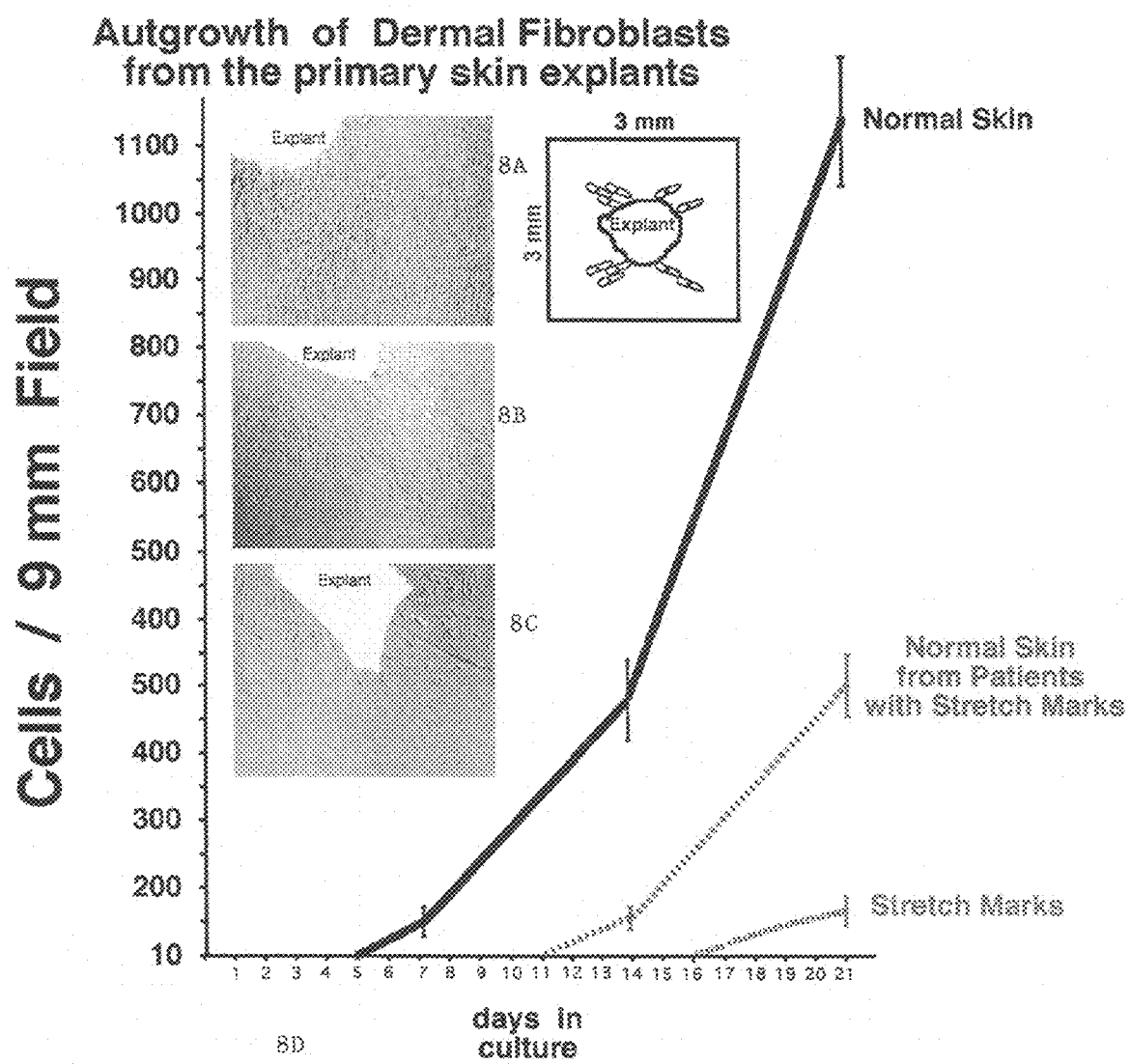
FIG. 8. Displays phase-contrast micrographs and results of assay measuring the initial outgrowth of fibroblasts from the primary explants of the skin biopsies demonstrate that in contrast to biopsies of the normal skin (A), in which fibroblast started to migrated within the first week in culture, the biopsies of healthy looking skin from individuals with the stretch marks (B) and biopsies derived from the actual stretch marks (C) demonstrated a significantly delayed (6 and 11 days, respectively) and less efficient fibroblasts outgrowth.
Figure 9:
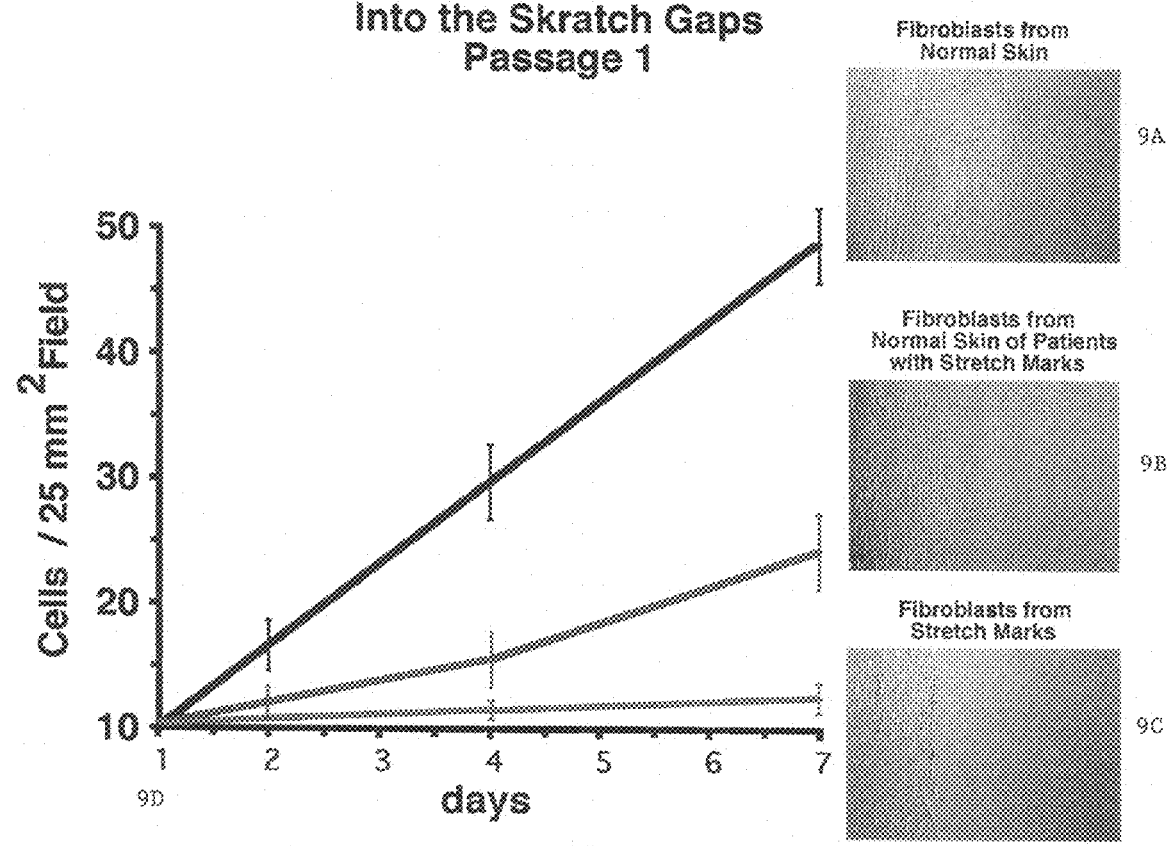
FIG. 9. Displays the phase-contrast micrographs and results of the quantitative assay of fibroblast migration into the scratch-gap performed in secondary cultures (passage 1) demonstrate that fibroblasts derived from normally-looking skin of patients with stretch marks, (B), and fibroblasts from the stretch marked skin (C) demonstrate slower migration rates as compared to fibroblasts derived from volunteers with no history of stretch marks (A).
Figure 10:
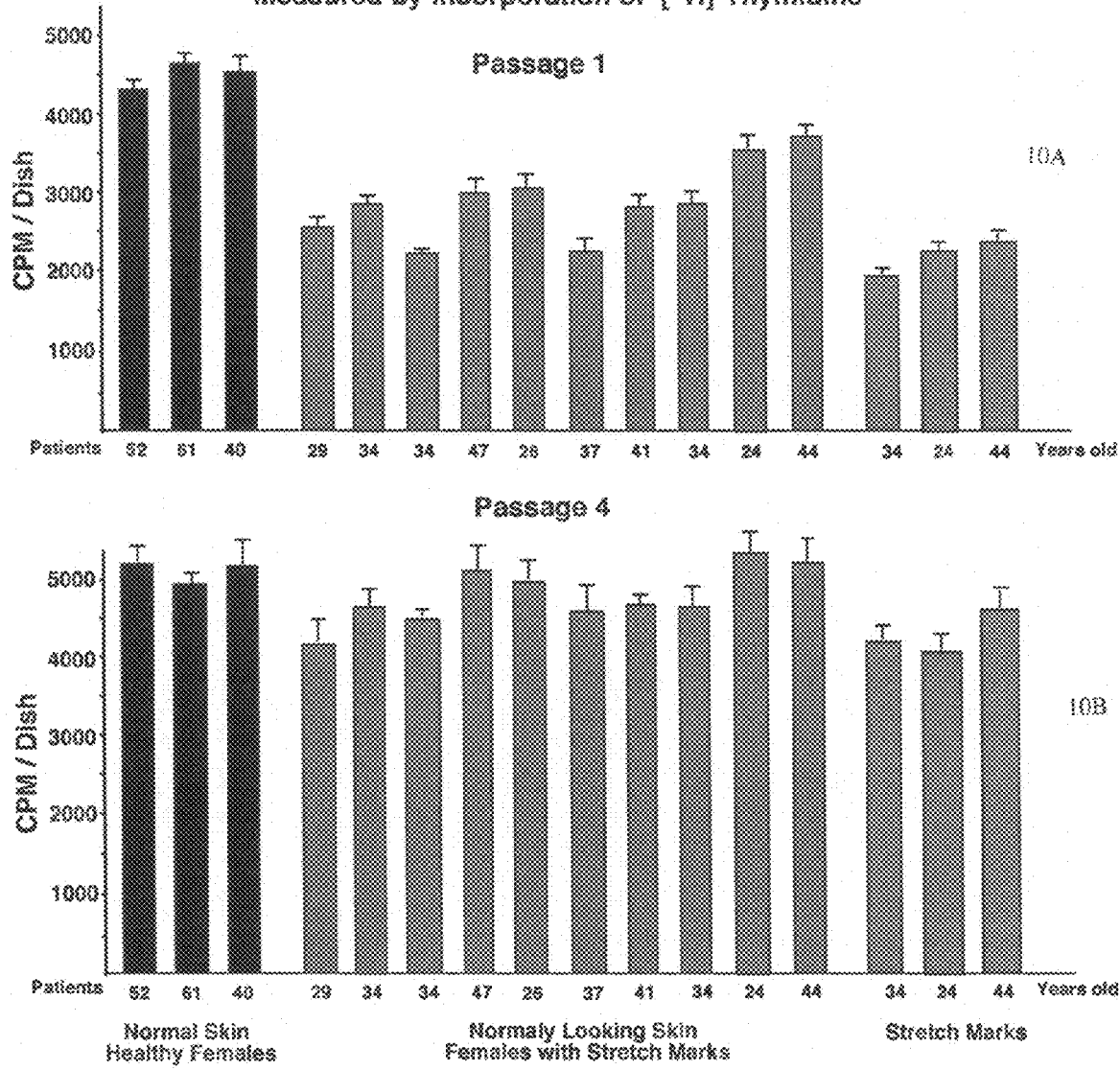
FIG. 10. Displays the results of the quantitative assay of cellular proliferation measured by $[^3H]$-thymidine incorporation into the secondary cultures of biopsy-derived fibroblasts in passage 1 (10A) and passage 4 (10B).

Monitoring of the initial outgrowth of fibroblasts from the primary explants of the skin biopsies demonstrated that in contrast to biopsies of normal skin, in which fibroblast started to migrate within the first week in culture, the biopsies of normally looking skin from individuals with the stretch marks (FIG. 8B) and biopsies derived from the actual stretch marks (FIG. 8C) demonstrated a significantly delayed (6 and 11 days, respectively) and less efficient fibroblast outgrowth (FIG. 8D). Moreover, results of the scratch-gap migration assay (FIG. 9D) and proliferation assays (FIG. 10A) performed in secondary cultures (passage 1) confirmed that fibroblasts derived from normally-looking skin of patients with stretch marks and fibroblasts from the stretch marked skin maintained their proportionally slower migration and proliferation rates as compared to fibroblasts derived from volunteers with no history of stretch marks.

Figure 11:
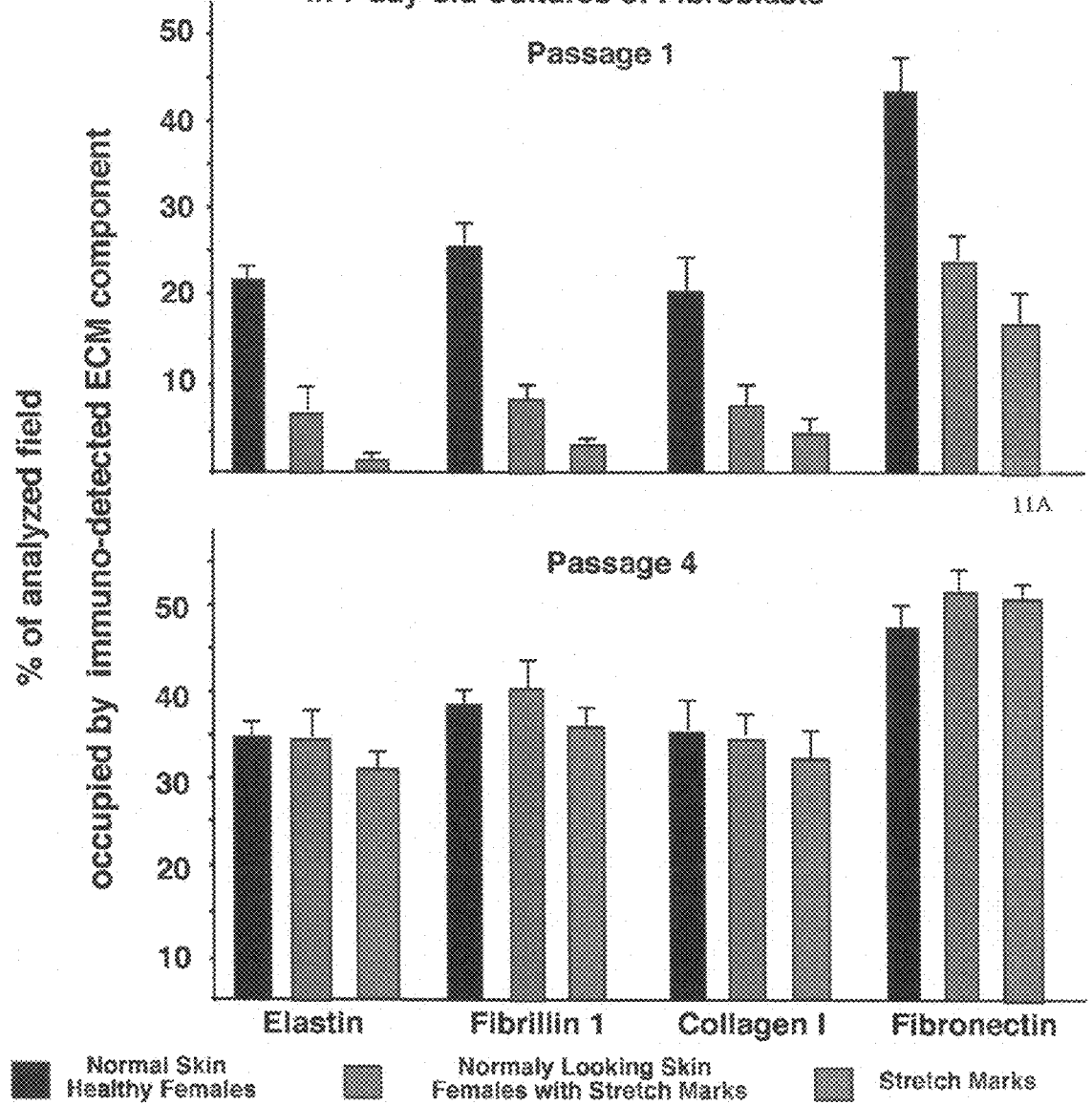
FIG. 11. (A) Results of quantitative morphometric analysis of immuno-stained 7 day-old cultures of fibroblasts from the first passage demonstrate that fibroblasts derived from normally-looking skin of patients with stretch marks, and fibroblasts from the stretch marked skin clearly produce proportionally less ECM than fibroblasts derived from individuals with no stretch marks. (B) Results of morphometric analysis of the fourth passage cultures demonstrate similar rather equal levels of all immuno-detectable ECM components.

Results of quantitative morphometric analysis of immuno-stained 7 day-old cultures of fibroblasts (first passage) derived from normal-looking skin of patients with stretch marks, and fibroblasts from stretch marked skin clearly demonstrated that cells from both experimental groups produce proportionally less ECM than fibroblasts derived from individuals with no stretch marks (FIG. 11A). The final production of elastic fibers by fibroblasts deriving from normal looking skin of patients with stretch marks did not exceed 20-30% of normal values. Fibroblasts from actual stretch marks did not deposit immuno-detectable elastic fibers (FIG. 12C).

Figure 12:
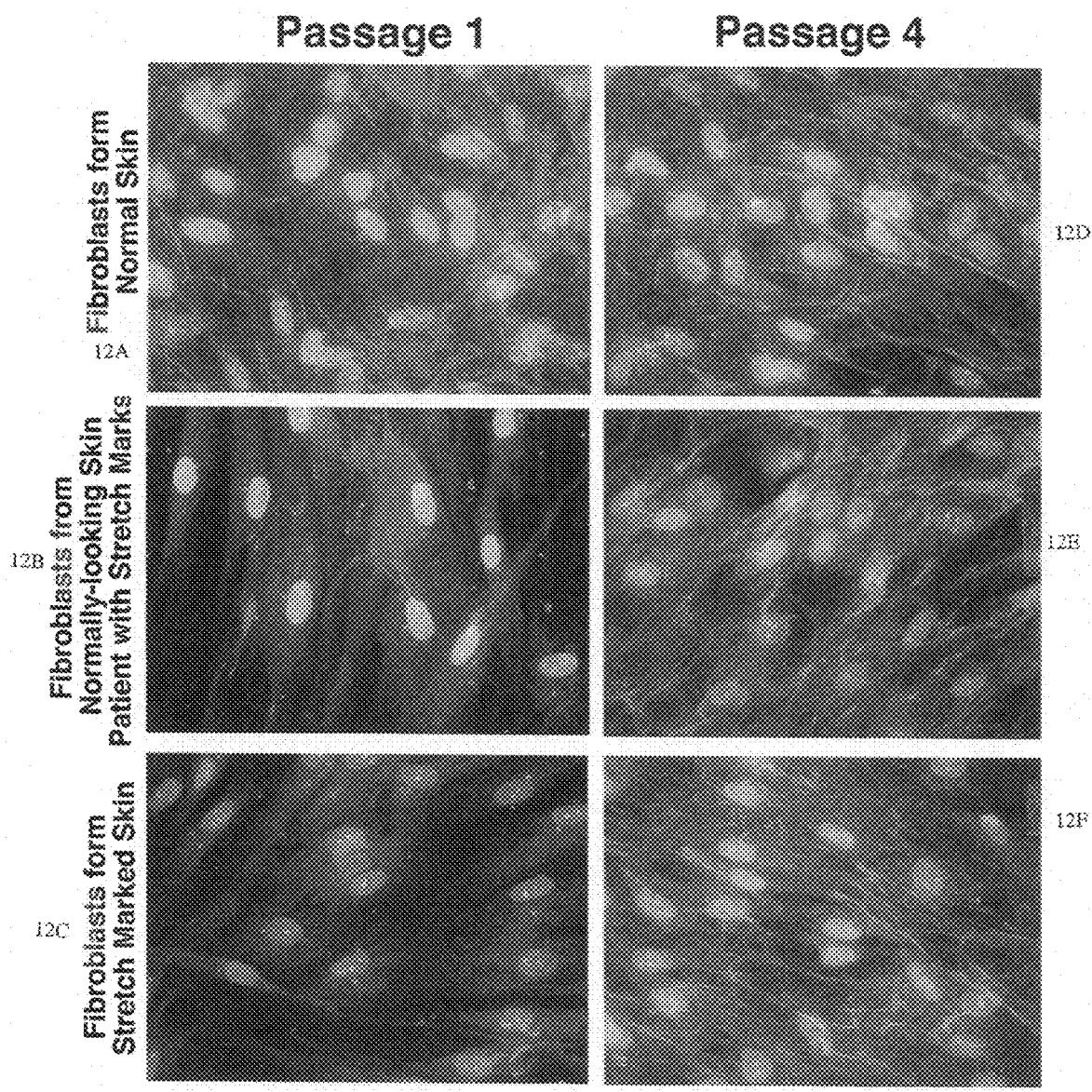
FIG. 12. Representative micrographs demonstrating immuno-detectable elastic fibers in 7 day-old cultures of biopsy-derived fibroblasts (passage 1) in normal skin (12A), normal-looking skin with stretch marks (12B) and stretch marked skin (12C) and passage 4 in normal skin (12D), normal-looking skin with stretch marks (12E) and stretch marked skin (12F). The first passage cultures of fibroblasts derived from normally-looking skin of patients with stretch marks (12B) produced fewer elastic fibers than normal fibroblasts (12A). Fibroblast derived from the stretch marked skin (12C) did not deposit immuno-detectable elastic fibers. The fourth passage fibroblasts derived from all experimental groups (12C, D, E) produce similar levels of elastic fibers.

It is also noteworthy that in 7 cases, out of 10 tested, dermal fibroblasts derived from patients with stretch marks demonstrated "recovery" in their proliferation rate and matrix production to the levels observed in cultures of normal skin fibroblasts, when maintained for several weeks (passage 4) in medium with 10% FBS alone (FIG. 11B and FIG. 12D). The lower than normal production of elastic fibers in the passage 1 of fibroblasts derived from normally-looking skin of patients with stretch marks (FIG. 13A), and fibroblasts from the stretch marked skin as well as, recovery of their elastogenic potentials in passage 4 was also confirmed by biochemical assay of insoluble elastin metabolically labeled with [$^3$H]-valine (FIG. 13B).

Results from a complete blood count and blood chemistry panels revealed values within normal ranges for all subjects. None of the patients indicated a history of dermatological problems or underlying genetic or metabolic systemic physiological conditions. None of the subjects were actively taking prescription medications.

Although the present invention has been described in considerable detail with reference to certain preferred embodiments thereof, other versions are possible. Therefore the spirit and scope of the appended claims should not be limited to the description and the preferred versions contained within this specification.

What is claimed is:

1. A method of screening for the increased potential for the development of new stretch marks in a human patient who already has stretch marks in one area of the skin comprising:
    establishing a total extracellular matrix protein content and a total fibroblast DNA content for normal dermal tissue from a control human subject;
    obtaining a sample of dermal tissue from non-stretch marked skin of said human patient;
    determining the total extracellular matrix protein content and the total fibroblast DNA content from said sample of dermal tissue from the human patient;
    comparing the extracellular matrix protein content and the fibroblast DNA content from said sample of dermal tissue from said human patient with the extracellular matrix protein content and the fibroblast DNA content for normal dermal tissue from said control subject; and
    determining an increased potential that the patient is predisposed for developing stretch marks when the sample of dermal tissue from said human patient has at least 36% less total extracellular matrix protein content and at least 16% less total fibroblast DNA content than the normal dermal tissue from said control subject.

2. The method of claim 1, wherein the total extracellular matrix protein is selected from elastin, collagen, fibrillin or a combination thereof.

3. The method of claim 1 further comprising:
    establishing a rate of proliferation for fibroblasts for nominal dermal tissue from a control human subject;
    determining a rate of proliferation for fibroblasts from said sample of dermal tissue from said human patient;
    comparing the rate of proliferation for fibroblasts from said sample of dermal tissue from said patient with the rate of proliferation for fibroblasts for normal dermal tissue from said control subject; and
    determining an increased potential that the patient is predisposed for developing stretch marks when the sample of dermal tissue from the patient has a lower rate of fibroblast proliferation than the normal dermal tissue.

4. The method of claim 1 further comprising:
    establishing a rate of migration for fibroblasts for normal dermal tissue from a control human subject;
    determining a rate of migration for fibroblasts from said sample of dermal tissue from said human patient;
    comparing the rate of migration for fibroblasts from said sample of dermal tissue from the patient with the rate of migration for fibroblasts for normal dermal tissue; and
    determining an increased potential that the patient is predisposed for developing stretch marks when the sample of dermal tissue from the patient has a lower rate of fibroblast migration than the normal dermal tissue.

5. The method of claim 1 further comprising:
    establishing a rate of the total extracellular matrix deposition for fibroblasts for normal dermal tissue from a control human subject;
    determining a rate of the total extracellular matrix deposition for fibroblasts from said sample of dermal tissue from said human patient;
    comparing the rate of the total extracellular matrix deposition for fibroblasts from said sample of dermal tissue from said patient with the rate of the total extracellular matrix deposition for fibroblasts for normal dermal tissue from said control subject; and determining an increased potential that the patient is predisposed for developing stretch marks when the sample of dermal tissue from the patient has a lower rate of fibroblast extracellular matrix deposition than the normal dermal tissue.

6. The method of claim 5, wherein the rate of the total extracellular matrix deposition is the rate of total elastin deposition.

7. The method of claim 6, wherein the rate of total elastin deposition in the sample of dermal tissue from said human patient does not exceed 30% of the rate of total elastin deposition in the normal dermal tissue sample from said control subject.

* * * * *

UNITED STATES PATENT AND TRADEMARK OFFICE
CERTIFICATE OF CORRECTION

| | |
|---|---|
| PATENT NO. | : 7,745,225 B2 |
| APPLICATION NO. | : 11/141635 |
| DATED | : June 29, 2010 |
| INVENTOR(S) | : Thomas Mitts |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 303 days.

Signed and Sealed this
Fifth Day of July, 2011

David J. Kappos
*Director of the United States Patent and Trademark Office*